(12) United States Patent
Lautner et al.

(10) Patent No.: US 11,439,609 B2
(45) Date of Patent: Sep. 13, 2022

(54) NITRIC OXIDE RELEASING PLGA MICROSPHERES FOR BIOMEDICAL APPLICATIONS

(71) Applicant: THE REGENTS OF THE UNIVERSITY OF MICHIGAN, Ann Arbor, MI (US)

(72) Inventors: Gergely Lautner, Ann Arbor, MI (US); Steven P. Schwendeman, Ann Arbor, MI (US); Mark E. Meyerhoff, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 208 days.

(21) Appl. No.: 15/735,122

(22) PCT Filed: Jun. 10, 2016

(86) PCT No.: PCT/US2016/036904
§ 371 (c)(1),
(2) Date: Dec. 8, 2017

(87) PCT Pub. No.: WO2016/201237
PCT Pub. Date: Dec. 15, 2016

(65) Prior Publication Data
US 2019/0307710 A1    Oct. 10, 2019

Related U.S. Application Data

(60) Provisional application No. 62/174,200, filed on Jun. 11, 2015.

(51) Int. Cl.
*A61K 31/19* (2006.01)
*A61K 47/36* (2006.01)
(Continued)

(52) U.S. Cl.
CPC ............ *A61K 31/19* (2013.01); *A61K 9/0014* (2013.01); *A61K 9/0024* (2013.01); *A61K 9/06* (2013.01);
(Continued)

(58) Field of Classification Search
CPC .. A61K 9/1647; A61K 9/5031; A61K 9/0014; A61K 9/06; A61K 47/36;
(Continued)

(56) References Cited

U.S. PATENT DOCUMENTS 5,116,861 A * 5/1992 Goto ..................... C07C 381/00
514/238.2
5,187,305 A  2/1993 Thompson et al.
(Continued)

FOREIGN PATENT DOCUMENTS

WO   WO 2010/005687   1/2010
WO   WO 2014/052443   4/2014

OTHER PUBLICATIONS

International Search Report and Written Opinion for International Application No. PCT/US2016/036904 dated Sep. 9, 2016, 10 pages.
(Continued)

*Primary Examiner* — Hong Yu
(74) *Attorney, Agent, or Firm* — Dierker & Kavanaugh, P.C.

(57) ABSTRACT

A polymeric composition includes poly(lactide-co-glycolide) (PLGA) microspheres; and at least one of a discrete RSNO adduct or a polymeric RSNO encapsulated within the microspheres, with the at least one of the discrete RSNO adduct or the polymeric RSNO adduct capable of releasing nitric oxide (NO). The polymeric composition exhibits stability under dry conditions at 37° C. and prolonged and controllable NO release rates, when exposed to light capable of photolyzing an RSNO bond, or when exposed to mois-
(Continued)

ture, for a predetermined amount of time from the at least one of the discrete RSNO adduct or the polymeric RSNO adduct.

17 Claims, 12 Drawing Sheets

(51) Int. Cl.
    *A61K 9/00*     (2006.01)
    *A61K 9/06*     (2006.01)
    *A61L 15/28*     (2006.01)
    *A61L 15/52*     (2006.01)
    *A61K 9/16*     (2006.01)

(52) U.S. Cl.
    CPC ............ *A61K 9/1647* (2013.01); *A61K 47/36* (2013.01); *A61L 15/28* (2013.01); *A61L 15/52* (2013.01); *A61L 2300/114* (2013.01)

(58) Field of Classification Search
    CPC ....... A61K 9/0024; A61K 31/19; A61L 15/28; A61L 2300/114; A61L 15/52
    See application file for complete search history.

(56) References Cited

U.S. PATENT DOCUMENTS

| | | | | |
|---|---|---|---|---|
| 5,405,919 | A | * | 4/1995 | Keefer .................. A61K 31/655 525/377 |
| 5,691,423 | A | * | 11/1997 | Smith .................. A61K 31/785 525/377 |
| 6,143,037 | A | * | 11/2000 | Goldstein ........... A61F 2/30767 424/422 |
| 2007/0243224 | A1 | * | 10/2007 | Ludwig ................. A61L 29/16 424/423 |
| 2007/0243262 | A1 | * | 10/2007 | Hurley ..................... A61P 9/00 424/499 |
| 2008/0099938 | A1 | | 5/2008 | Mandal et al. |
| 2012/0136323 | A1 | | 5/2012 | Stasko et al. |

OTHER PUBLICATIONS

Do, Y.S et al., "In-stent restenosis limitation with stent-based controlled-release nitric oxide: Initial results in rabbits", Radiology [online], Feb. 2004 (Feb. 2004) [Retrieved on Aug. 12, 2016], vol. 230, Issue 2, retrieved from the Internet: <DOI: 10.1148/radiol. 2302020417>, pp. 377-382; see entire document, especially p. 378.
Naghavi, N et al., "Nitric Oxide Donors for Cardiovascular Implant Applications", Small [online], Jan. 14, 2013 (Jan. 14, 2013) [Retrieved on Aug. 12, 2016], vol. 9, Issue 1, retrieved from the Internet: <DOI: 10.1002/smll.201200458>, pp. 22-35; see entire document, especially p. 28.

* cited by examiner

NITRIC OXIDE RELEASING PLGA MICROSPHERES FOR BIOMEDICAL APPLICATIONS

CROSS-REFERENCE TO RELATED APPLICATIONS

This application claims the benefit of U.S. provisional application Ser. No. 62/174,200, filed Jun. 11, 2015, the contents of which is incorporated by reference herein in its entirety.

STATEMENT REGARDING FEDERALLY SPONSORED RESEARCH OR DEVELOPMENT

This invention was made with government support under Grant No. EB-000783 awarded by the National Institutes of Health (NIH). The government has certain rights in the invention.

BACKGROUND

Nitric oxide (NO) is a fascinating and important endogenous free-radical gas with potent antimicrobial, vasodilating, smooth muscle relaxant, and growth factor stimulating effects. The efficiency of gaseous NO as a therapeutic agent (e.g., administered topically for dermatological or inhaled for pulmonary treatments) is already proven, however its applicability may be hindered by its cumbersome administration and short lifetime. To overcome the drawbacks of the gaseous NO, donor molecules have been described and developed in the literature such as, e.g., metal nitrosyls, N-nitroso compounds, C-nitroso compounds, and S-nitrosothiols (RSNOs), organic nitrites and nitrates, and N-diazeniumdiolates (NONOates). However, the administration of NO donors and their targeting is still troublesome due to their low stability (e.g., NO is unstable especially in biological environments), along with their potential side-effects.

BRIEF DESCRIPTION OF THE DRAWINGS

Features of examples of the present disclosure will become apparent by reference to the following detailed description and drawings, in which:

(FIGS. 3A and 3E) blank, (FIG. 3B) 7.4 (±0.3) %, (FIG. 3C) 9.1(±0.3%), (FIG. 3D) 12.4(±0.2) %, (FIG. 3F) 6.3(±0.2%), (FIG. 3G) 8.5(±0.7%), (FIG. 3H) 11.7(±0.8%), all as wt %, scale bar is 10 μm;

DETAILED DESCRIPTION

The preparation of nitric oxide (NO) releasing biodegradable poly(lactic-co-glycolic acid) (PLGA) microspheres and their possible use in biomedical applications are disclosed herein.

Figure 1:
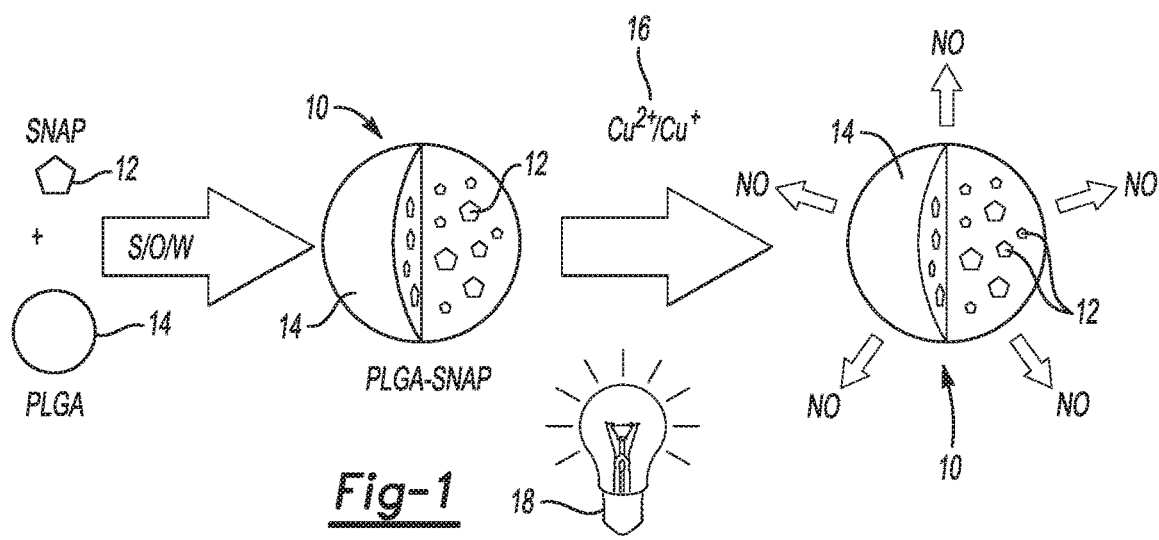
FIG. 1 is a perspective, partially cross-sectioned schematic flow diagram showing an example of a polymeric composition and its use according to an example of the present disclosure.

Referring now to FIG. 1, a polymeric composition according to an example is designated generally at 10. Examples of the polymeric composition 10 include encapsulation of an S-nitroso species (e.g., S-nitroso-N-acetylpenicillamine (SNAP)) 12 in biodegradable poly(lactic-co-glycolic acid) (PLGA) microspheres (PLGA-SNAP) 14, which release nitric oxide (NO) for, e.g., weeks in a continuous and controlled manner. The rate and duration of released NO are tunable by varying the degree of SNAP loading within the microspheres, and the type/nature of the PLGA (e.g., acid terminated or ester-capped, lactic-glycolic acid ratio, etc.). The NO release rate also can be tuned to desired levels by use of copper ions (the source of copper ions schematically shown and designated at 16) or light (the source of light schematically shown and designated at 18)—the present inventors have found that, for significant NO release, the microspheres can be exposed to copper ions in solution, or their NO emission can be induced and modulated by light even in dry state or also in solution. The dry PLGA-SNAP microspheres are highly stable microparticles that retain their NO release properties since they have an excellent storage stability at room temperature in the dark.

No SNAP-doped PLGA microspheres have been reported in the literature thus far. Non-degradable silicon particles as a carrier and NONOates as NO donors (commercially available as NITRICIL™ from Novan Inc.) have been proposed; however, NONOates are known to form carcinogenic nitrosamines in some instances. Another issue with prior efforts to make particle type NO donors is that since the NO donors are immobilized on the surface of the particles, they are exposed to the matrix environment. Hence, the presence of small amounts of ascorbate or copper ions can induce NO burst type release, which can potentially cause adverse effects.

In contrast, examples of the PLGA-SNAP microspheres of the present disclosure are advantageous in that PLGA is completely biodegradable. An aim of the present disclosure was to develop a particle-based NO release material that could yield physiologically relevant levels of NO for extended periods (e.g., 1-2 weeks), while minimizing risk of toxic by-products. This is possible since the product of NO loss from S-nitroso-N-acetyl-penicillamine (SNAP) (the NO donor used in examples of this disclosure), is N-acetyl-penicillamine (NAC), which is non-toxic at low levels. The precursor of the NO donor SNAP (i.e., penicillamine itself (after loss of an acetate group from NAC) is an FDA approved drug for reversing heavy metal ion poisoning.

NO is useful in biomedical applications, such as, e.g., in wound healing, since NO has substantial antimicrobial effects and promotes growth of new blood vessels. To prepare a new type of NO releasing wound dressing, in an example, the PLGA-SNAP microspheres were incorporated into alginate hydrogel films (PLGA-SNAP/alginate) which can be cross-linked with copper(II) ions. Alginate hydrogels are used for wound healing purposes; however, the most often used cross-linker is calcium(II). Copper(II) cross-linked alginate gels are reported in the literature for wound healing; however, in examples of the present disclosure, it is not the copper(II) itself that promotes the wound healing, but rather, the copper(II) induces the NO release from the PLGA-SNAP microspheres. The PLGA-SNAP/alginate film continuously releases NO at endothelial level over a week period. These PLGA-SNAP/alginate films may be used as wound dressings for skin burns and chronic wounds (e.g., diabetic ulcers, pressure ulcers, etc.), where the antimicrobial and wound healing effects of NO are advantageous.

In another example, the PLGA-SNAP microspheres may be dispersed in ointments to treat dermal diseases and promote wound healing. The NO release from microspheres dispersed in hydrophobic ointments (e.g., petroleum jelly, etc.) may be induced by an external light source.

In a further example, the PLGA-SNAP microspheres may be incorporated into an NO releasing depot injection. A depot injection is an injection that deposits a drug in a localized mass (called a depot). The depot is gradually resorbed by surrounding tissue.

Nitric oxide (NO) has been found to be one of two potent vasodilators secreted by normal endothelium that has the ability to inhibit platelet adhesion/activation and aggregation to the blood vessel wall. The NO-flux from a normal and stimulated endothelium has been estimated to be in the range of $0.5 \times 10^{-10}$ mol cm$^{-2}$ min$^{-1}$ to $4 \times 10^{-10}$ mol cm$^{-2}$ min$^{-1}$. Nitric oxide has been extensively studied for its inhibitory effects on circulating platelet and monocyte activation that leads to aggregation and ultimately initiation of thrombosis. A wide range of NO donors such as S-nitrosothiols (RS-NOs), N-Hydroxy-N-nitrosoamines, N-diazeniumdiolates and nitrosyl metal complexes have been studied at least over the past decade.

Nitric oxide (NO) can be released from an NO adduct/donor species encapsulated within poly(lactide-co-glycolide) (PLGA) microspheres. "Nitric oxide adducts" (NO adducts) and "NO-donors" refer to compounds and functional groups which, under physiological conditions, can donate and/or release NO such that biological activity of the NO is expressed at the intended site of action/target site.

Suitable NO adducts (examples of which include discrete adducts) for examples of the polymeric composition as disclosed herein are generally those exhibiting capability of being encapsulated within the PLGA microspheres and exhibiting process preparation stability.

"Discrete NO adducts" as referred to herein are those NO adducts (examples of which are RSNOs) which, when incorporated into the PLGA microspheres, release therapeutically relevant fluxes of NO, ranging from about $0.2 \times 10^{-10}$ mol cm$^{-2}$ min$^{-1}$ to about $20 \times 10^{-10}$ mol cm$^{-2}$ min$^{-1}$ of NO from the polymer phase. As used herein, those compounds that have their NO-releasing moiety covalently attached to a biodegradable polymer backbone are generally referred to as "polymeric NO adducts." Examples of suitable polymeric NO adducts include, but are not limited to, S-nitrosothiolated biodegradable polymers. Some examples of biodegradable polymers include poly(esters) based on polylactide (PLA), polyglycolide (PGA), polycaprolactone (PCL), and their copolymers, as well as mixtures thereof. Some examples of the discrete NO adducts exhibit some lipophilicity, but may be made more lipophilic by derivatization with one or more alkyl groups.

Various biodegradable polymer materials may be employed in examples of the polymeric NO adducts as disclosed herein. The polymer of choice will be one capable of releasing NO from, for example, covalently attached and/or dispersed S-nitrosothiol (RSNO) type NO-adducts within the polymer. The polymer of choice may also depend upon the application in which the polymeric composition will be used and the desired NO release rate for that application. As examples, a polymer having higher water uptake may be suitable in applications where quick NO release is desirable, while a polymer having lower water uptake may be suitable in applications where slow NO release is desirable.

The PLGA microspheres assist in prolonging NO release by creating an acidic environment to further stabilize the RSNO species. The limited solubility of the RSNO may also prevent early release by limiting the mobility reactants in the solid state necessary to generate NO.

Further, a system is contemplated as being within the purview of the present disclosure that includes discrete RSNOs encapsulated within PLGA microspheres, and/or a biodegradable polymer having RSNO appended thereto (e.g., by covalent attachment) encapsulated within the PLGA microspheres. For example, previously prepared biodegradable polymers with appended RSNO functional groups can be mixed with discrete RSNOs or similar species to create the long-term NO release PLGA microspheres enabled by the present disclosure.

In some examples, the NO adduct of choice is one capable of spontaneous release of NO when the polymer is exposed to solutions and/or blood under physiological conditions. In other examples, the NO adduct of choice is one capable of spontaneous release of gas phase NO when the polymer is exposed to certain light conditions. Some examples of NO adducts include discrete S-nitrosothiols (RSNOs).

It is believed that examples of the present disclosure including SNAP encapsulated within PLGA microspheres may help stabilize the RSNO adduct, thus advantageously allowing longer NO release from the RSNO species and enhanced storage stability, even at higher temperatures (e.g., 37° C.).

Spontaneous release of NO from the polymer may be governed by at least one process occurring between the NO adduct and the surrounding environment. For RSNO species, these include, but are not limited to temperature, moisture, and the presence of certain wavelengths of light. For example, photolysis of the S—N bond in the RSNO species liberates NO gas. Photolysis can occur with light in either the 300 nm to 400 nm wavelength range or the 500 nm to 600 nm wavelength range. In this example, the efficiency of NO release is generally greater in the higher wavelength range.

It is to be understood that discrete nitric oxide adducts may be encapsulated within the PLGA microspheres. Some examples of discrete RSNOs include, but are not limited to S-nitrosoglutathione (GSNO), S-nitroso-N-acetylpenicillamine (SNAP), S-nitrosocysteine (CysNO), etc., and derivatized discrete RSNOs. Derivatized RSNOs may be modified with alkyl group(s). As examples, a derivative may have an alkyl group attached to the free carboxyl group of SNAP and/or may have a longer alkyl (i.e., longer than acetyl) attached to the amine group of S-nitrosopenicillamine. As an example, an ester linkage may be formed between the desired alkyl group and the free carboxyl group of SNAP. As another example, a long chain alkyl (including from 4 to 20 carbon atoms) may replace the acetyl group of SNAP so that the long chain alkyl is attached to the amine nitrogen. As other examples, a sugar may be attached to the carboxyl group of SNAP (e.g., glucose-SNAP, mannose-SNAP, fructose-SNAP, etc.).

As mentioned above, nitric oxide exhibits antimicrobial activity, including killing bacteria and preventing biofilm formation. Bacterial infections and biofilm formation are problems that can cause complications with biomedical devices. Bacteria also possess the ability to form biofilms on surfaces when the organism secretes a polysaccharide matrix in which the bacteria will live. This matrix provides both nutrients and protection against the host defense and antibiotics. Biofilms can act as a source of chronic infection, thereby prolonging the recovery time. Among its many biological roles, nitric oxide functions as an antimicrobial agent and as an accelerant to the wound healing process. Nitric oxide has broad-spectrum antibacterial properties, killing both gram-positive and gram-negative bacteria. Low levels of nitric oxide are also reported to efficiently disperse biofilms that have formed on the surface of indwelling medical devices.

In order to avoid the continuous infusion of RSNO species, the present disclosure includes PLGA polymers that are capable of storing RSNO species. The PLGA microspheres having RSNO encapsulated therein according to examples of the present disclosure can advantageously release NO, as well as potentially supplement the endogenous RSNO levels, if NO generating catalysts are also employed. For example, endogenous ascorbic acid may be present in blood/interstitial fluid at a sufficient level in order to efficiently catalyze decomposition of released RSNO.

To further illustrate the present disclosure, various examples are given herein. It is to be understood that these examples are provided for illustrative purposes and are not to be construed as limiting the scope of the present disclosure.

EXAMPLES

In the present disclosure, to ultimately develop site-specific controlled release vehicles for NO, the NO donor S-nitroso-N-acetyl-D-penicillamine (SNAP) was encapsulated within poly(lactic-co-glycolic acid) 50:50 (PLGA) microspheres by using a solid-in-oil-in-water emulsion solvent evaporation method. The highest payload was 0.56 (±0.01) mol SNAP/mg microspheres. The release kinetics of the donor were controlled by the bio-erosion of the PLGA microspheres. By using an uncapped PLGA ($M_w$=24,000-38,000), SNAP was slowly released for over 10 days, whereas by using the ester capped PLGA ($M_w$=38,000-54,000), the release lasted for over 4 weeks. The presence of copper ions and/or ascorbate in solution efficiently decomposed the released NO donor to obtain sustained NO release. It was also demonstrated that light can be used to induce rapid NO release from the microspheres over several hours. SNAP exhibited excellent storage stability when encapsulated in the PLGA microspheres. Examples of the new microsphere formulations of the present disclosure may be useful for site-specific administration and treatment of pathologies associated with dysfunction in endogenous NO production, e.g., treatment of diabetic wounds (as mentioned above), or in diseases involving other biological functions of NO including vasodilation, antimicrobial, anticancer, and neurotransmission functions.

Materials and Methods

PLGA (RG 503H and RG 504) was obtained from Evonik Industries (Essen, Germany). Reagents, buffer salts, poly (vinyl alcohol) (PVA, $M_w$: 9,000-10,000, 80% hydrolyzed) and solvents were ordered from Sigma-Aldrich. All chemicals were used as received. All aqueous solutions were prepared with ultrapure deionized water (18.2 MΩ cm resistivity, Millipore). Composition of PBS buffer was 0.01 M phosphate buffer, 0.0027 M potassium chloride and 0.137 M sodium chloride, pH 7.4. The PBSACu buffer contained 50 M $CuCl_2$ and 1 mM ascorbate in PBS. PBSE contained 0.1 mM EDTA in PBS. 50 mL amber polypropylene centrifuge tubes were used for in-vitro NO release experiments (Greiner Bio-One International, Kremsmünster, Austria).

S-Nitroso-N-acetyl-D-penicillamine (SNAP) Synthesis

Two grams of N-acetyl-D-penicillamine (NAP) (Fluka) was dissolved in a mixture of 50 mL methanol, 16.7 mL $H_2O$, 8.3 mL concentrated HCl and 2.5 mL concentrated $H_2SO_4$. Twenty mL of 1 M $NaNO_2$ was then slowly added to the mixture. The color of the solution turned dark red. The solution was placed onto an ice bath and with blowing $N_2$ over the solution so that the methanol can be evaporated until crystals formed (about 3 hours). The green crystals were collected by solution filtration, washed with ice-cold water and vacuum dried. The entire process was performed while protecting the solutions from light to avoid photodecomposition of SNAP. Before encapsulation into PLGA particles, the SNAP was ground by a CryoMill (Retsch, Düsseldorf, Germany). Five hundred mg of SNAP was ground in two 5 mL stainless steel jars, with 16 stainless steel (3 mm diameter) balls in each. After 8 minutes long precooling with liquid nitrogen at 5 Hz, the SNAP particles were ground for 40 minutes at 20 Hz, then freeze-dried (−41° C., 0.160 mbar) for 1 day after flash freezing in liquid nitrogen.

SNAP Loaded PLGA Microsphere Preparation

SNAP loaded microspheres were prepared by a solid-in-oil-in-water emulsion solvent evaporation technique described below (see also, e.g., C. Wischke, S. P. S. Schwendeman, Principles of encapsulating hydrophobic drugs in PLA/PLGA microparticles, International Journal of Pharmaceutics. 364 (2008) 298-327): PLGA polymer was dissolved in 1 mL of methylene-chloride in a 100 mm×16 mm glass culture tube. The cryomilled SNAP was added to this solution and homogenized at 10,000 rpm for 1 minute with a Tempest IQ$^2$ homogenizer (The VirTis Co., Gardiner, N.Y., USA) equipped with a 10 mm shaft. Four mL of a 5% (w/v) PVA in DI water was immediately pipetted in it and vortexed (Genie 2, Fisher-Scientific Industries, Inc., Bohemia, N.Y., USA) at the highest speed for 1 minute, then poured into 100 mL of 0.5% (w/v) PVA in DI water under rapid stirring with a magnetic stir-bar, and hardened for 3 hours. The resulting microspheres were sieved and washed with 500 mL DI water. The fraction of particles sieved in the range of 20 μm-125 μm was collected and freeze-dried (−41° C., 0.160 mbar) for 2 days after flash freezing in liquid nitrogen.

Measurement of Loading

To determine the SNAP loading in a given lot of microspheres, 5 mg of the microspheres were dissolved in 1 mL acetonitrile, and the concentration of SNAP was measured by UV/VIS absorbance analysis: absorbance at 340 nm was measured using a Synergy Neo Microplate Reader (BioTek U.S., Winooski, Vt., USA). The encapsulation efficiency was calculated as the ratio of the actual to the theoretical loading (based on total amount of SNAP used in the preparation).

To measure the SNAP remaining within the microspheres after soaking in buffer for given time periods, the microspheres were washed three times with 100 μM EDTA containing buffer and DI water to remove residual copper and buffer salts prior to dissolving them in acetonitrile, and measuring the absorbance at 340 nm.

Morphology and Size Distribution of Microspheres

For morphology and size distribution analysis, microspheres were coated with 40 nm of gold using a sputter coater (Desk II, Denton Vacuum Inc., Hill, N.J., USA) for 120 seconds. Secondary electron micrographs were taken by a Hitachi S-3200N Variable Pressure SEM (Hitachi High-Technologies Corp., Tokyo, Japan). The applied accelerating voltage was 15 kV. For size distribution measurements, the diameter of at least 500 particles was measured and analyzed with ImageJ software (see, e.g., C. A. Schneider, W. S. Rasband, K. W. Eliceiri, NIH Image to ImageJ: 25 years of image analysis, Nature Methods. 9 (2012) 671-675). For cross-sectional images, the microspheres were cut using a razor-blade on a glass slide prior to coating with gold for the SEM analysis.

To observe the morphology changes of the microspheres after soaking in buffer, the microspheres were washed three times with DI water after a given soaking time in order to remove salts prior to SEM analysis.

Nitric Oxide Release Measurement by Nitric Oxide Analyzer

For NO release experiments, 10 mg of microspheres were incubated in 5 mL of release media at 37° C. in an amber 50 mL centrifuge vial placed onto a rocker for gentle shaking during incubation at 37° C. Nitric oxide release was quantitated by using an ozone-based chemiluminescence technology with a Sievers Nitric Oxide Analyzer (NOA, Model 280i, GE Analytical Instruments, Boulder, Colo., USA). The amber incubation vials were thermostated at 37° C. using a water bath. Nitric oxide released from the suspension of particles was purged from the media via a $N_2$ purge gas (at about 50 mL/min) into the NOA system that had been pre-calibrated. The release media was changed every second day whenever NO release experiments were performed. The NO levels in ppb unit measured every other day were converted to an NO release rate in mol $min^{-1}$ $mg^{-1}$ unit using the NOA instrument constant determined by quantitative reduction of a known amount of nitrite. The amount of NO released was calculated by integration of NO release rate curves for given time periods, and the fraction of NO release was determined based on the initial predetermined SNAP loading into the microspheres.

Light modulated NO release measurements were performed by placing a given amount of the SNAP loaded PLGA particles into a transparent vial irradiated with a tungsten halogen lamp using a Fostec DCR II EKE cold light source (Schott-Fostec, LLC, New York, USA) set at the highest intensity.

Results and Discussion

Encapsulation of SNAP Into PLGA Microspheres

Figure 2A:
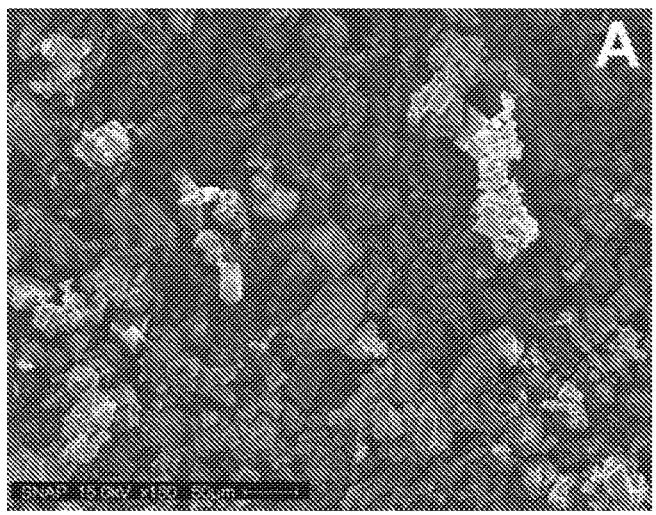
FIGS. 2A and 2B are scanning electron microscope (SEM) images of SNAP crystals before (FIG. 2A) and after (FIG. 2B) cryomilling.
Figure 2B:
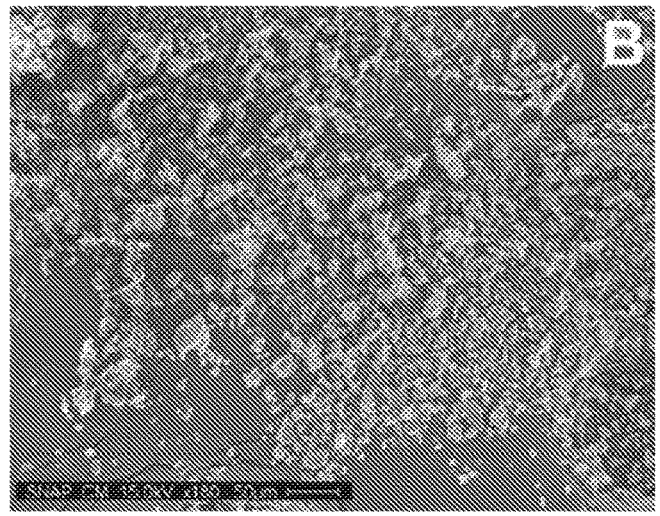
Figure 2C:
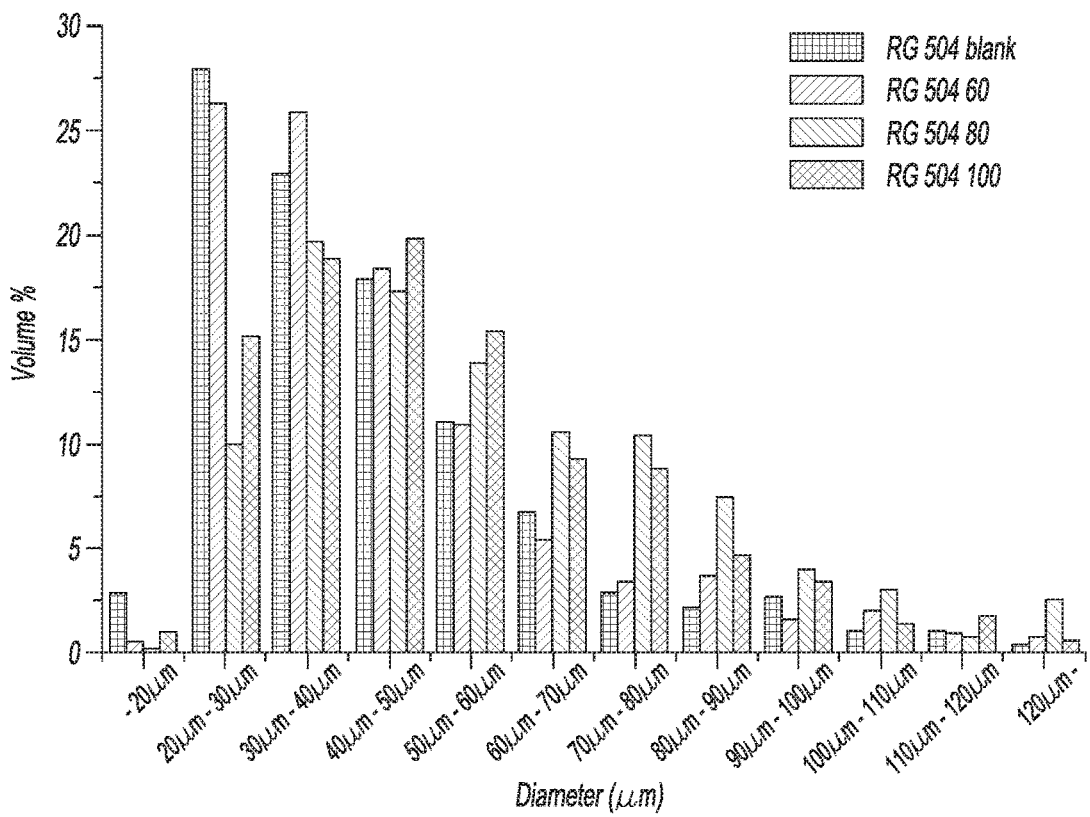
FIGS. 2C and 2D are graphs showing size distribution of the RG 504 (FIG. 2C) and RG 503H (FIG. 2D) PLGA-SNAP formulations based on SEM measurements (at least 500 particles/region/sample)
Figure 2D:
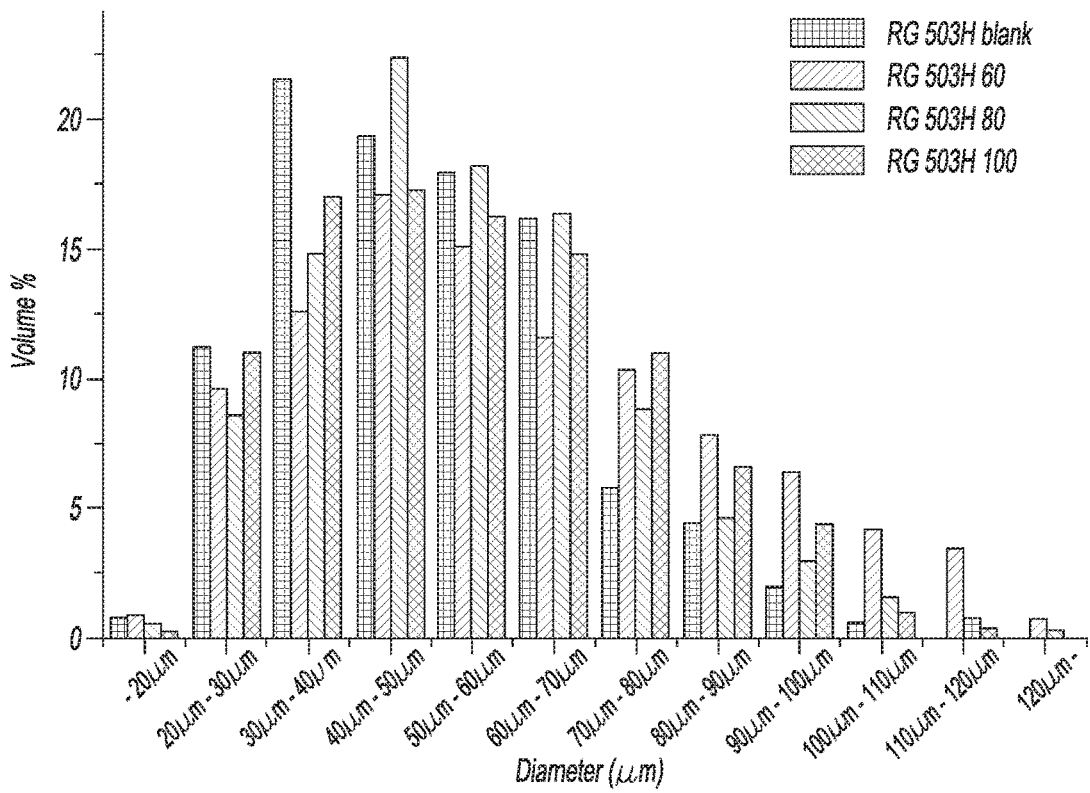
Figures 3A, 3B, 3C, 3D, 3E, 3F, 3G, 3H:
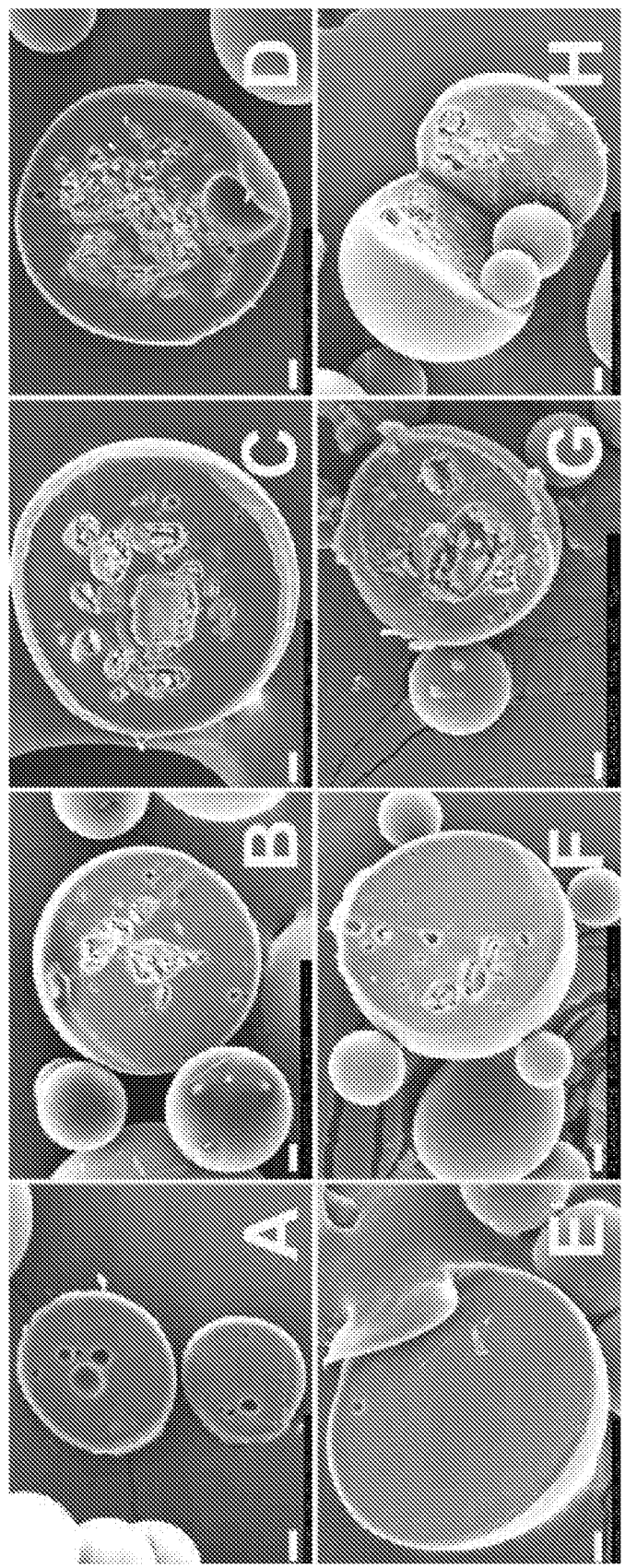
FIGS. 3A-3H are cross sectional secondary electron micrographs of RG 503H (FIGS. 3A-3D) and RG 504 (FIGS. 3E-3H) PLGA-SNAP microspheres with increasing SNAP loadings.

Before encapsulation, the dark green crystalline SNAP was micronized at −196° C. in a ball mill, resulting in a pale green powder of SNAP with particle dimensions typically <25 μm (see FIGS. 2A and 2B). For encapsulation, a faster degrading acid terminated PLGA (RG 503H) as well as a slower degrading ester capped PLGA (RG 504) were used, and both were a 50:50 ratio of lactic acid monomer to glycolic acid monomer. The polymers were dissolved in methylene chloride, which does not dissolve the NO donor SNAP. The solid in oil in water emulsion and solvent evaporation method (S/O/W) described in the Materials and Methods section provided encapsulation efficiencies of about 48-62% for SNAP (see Table 1), yielding pale green PLGA microspheres with diameters in the ~20 μm to ~125 μm size range (see FIG. 2C and FIG. 2D) after sieving. The SNAP loading of the PLGA microspheres was determined by UV/VIS absorption after dissolving the microspheres in acetonitrile. Increasing the amount of micronized SNAP in the formulation yielded increased SNAP loading with both PLGA polymers with values up to about 12% weight per weight (w/w).

TABLE 1

Formulations (S/O/W), loadings, encapsulation efficiency and particle size distribution

| Formulation | Molecular weight kDa | End group | PLGA mg/mL | SNAP mg | Loading[a] (w/w) % | Encapsulation efficiency % | D[4,3][b] μm |
|---|---|---|---|---|---|---|---|
| RG 503H blank | 24-38 | Free carboxylic acid | 400 | 0 | n.a. | n.a. | 68 |
| RG 503H 60 | 24-38 | Free carboxylic acid | 400 | 60 | 7.4(±0.3) | 56.3 | 88 |
| RG 503H 80 | 24-38 | Free carboxylic acid | 400 | 80 | 9.1(±0.3) | 53.9 | 75 |
| RG 503H 100 | 24-38 | Free carboxylic acid | 400 | 100 | 12.4(±0.2) | 61.9 | 76 |
| RG 504 blank | 38-54 | Ester | 400 | 0 | n.a. | n.a. | 84 |
| RG 504 60 | 38-54 | Ester | 400 | 60 | 6.3(±0.2) | 48.2 | 80 |

TABLE 1-continued

Formulations (S/O/W), loadings, encapsulation efficiency and particle size distribution

| Formulation | Molecular weight kDa | End group | PLGA mg/mL | SNAP mg | Loading$^a$ (w/w) % | Encapsulation efficiency % | D[4,3]$^b$ μm |
|---|---|---|---|---|---|---|---|
| RG 504 80 | 38-54 | Ester | 400 | 80 | 8.5(±0.7) | 50.7 | 88 |
| RG504 100 | 38-54 | Ester | 400 | 100 | 11.7(±0.8) | 58.5 | 81 |

$^a$(±standard deviation), n = 3
$^b$SEM, n = 500 particles/region/sample, D[4,3]: volume-based mean diameter Size distribution measurements were also performed by laser diffraction (Malvern Mastersizer 2000 equipped with Hydro 2000 S accessory, Worcestershire, UK) after an extended storage period at −20° C. (see Table 2). Particles were dispersed in water containing 0.02% PVA as a surfactant for these measurements and stirred at 2975 rpm. The associated refractive index and absorption values of PLGA were 1.59 and 0.01, respectively, and the refractive index of dispersant DI water was 1.33. For size distribution calculations, a model with irregular particle shape was considered.

TABLE 2

Size distribution data of formulations based on SEM measurements and on laser diffraction. Laser diffraction data were acquired after extended storage period in the freezer

| | SEM* | | | | Laser diffraction** | | | |
|---|---|---|---|---|---|---|---|---|
| Sample Name | D [4,3] - Volume weighted mean [μm] | d (0.2) [μm] | d (0.5) [μm] | d (0.8) [μm] | D [4,3] - Volume weighted mean [μm] | d (0.2) [μm] | d (0.5) [μm] | d (0.8) [μm] |
| RG 503H blank | 68 | 29 | 49 | 72 | 64 | 41 | 60 | 86 |
| RG 503H 60 | 88 | 38 | 56 | 83 | 80 | 58 | 77 | 101 |
| RG 503H 80 | 75 | 37 | 51 | 69 | 77 | 56 | 73 | 96 |
| RG 503H 100 | 76 | 36 | 52 | 74 | 78 | 54 | 74 | 100 |
| RG 504 blank | 84 | 27 | 38 | 58 | 73 | 47 | 68 | 97 |
| RG 504 60 | 80 | 27 | 38 | 56 | 79 | 48 | 73 | 109 |
| RG 504 80 | 88 | 35 | 52 | 78 | 76 | 44 | 70 | 107 |
| RG 504 100 | 81 | 32 | 49 | 73 | 87 | 48 | 76 | 120 |

*SEM, n = 500 particles/region/sample
**after extended storage period at −20° C.
D[4,3]: volume-based mean diameter, D(0.2): 20$^{th}$ volume percentile on a volume basis, D(0.5): 50$^{th}$ volume percentile on a volume basis, D(0.8): 80 volume percentile on a volume basis The amount of encapsulated SNAP was approximately 0.3-0.6 μmol per mg microsphere. FIGS. 3A-3H show the cross sectional SEM images of the microspheres with increasing SNAP loadings. The SNAP crystals are embedded typically in the center portion of the microspheres.

Figure 4A:
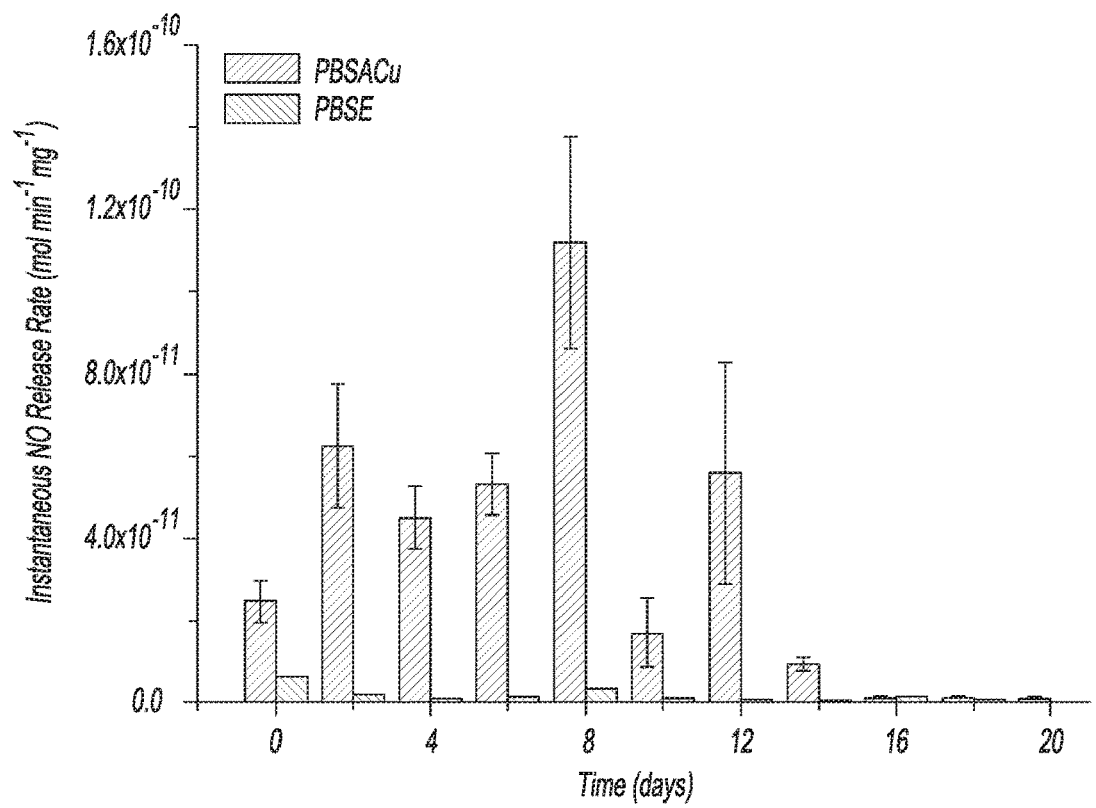
FIGS. 4A and 4B are graphs showing instantaneous NO release rates of highest loaded (FIG. 4A) RG 503H 100 and (FIG. 4B) RG 504 100 PLGA-SNAP microspheres in PBSACu and PBSE.
Figure 4B:
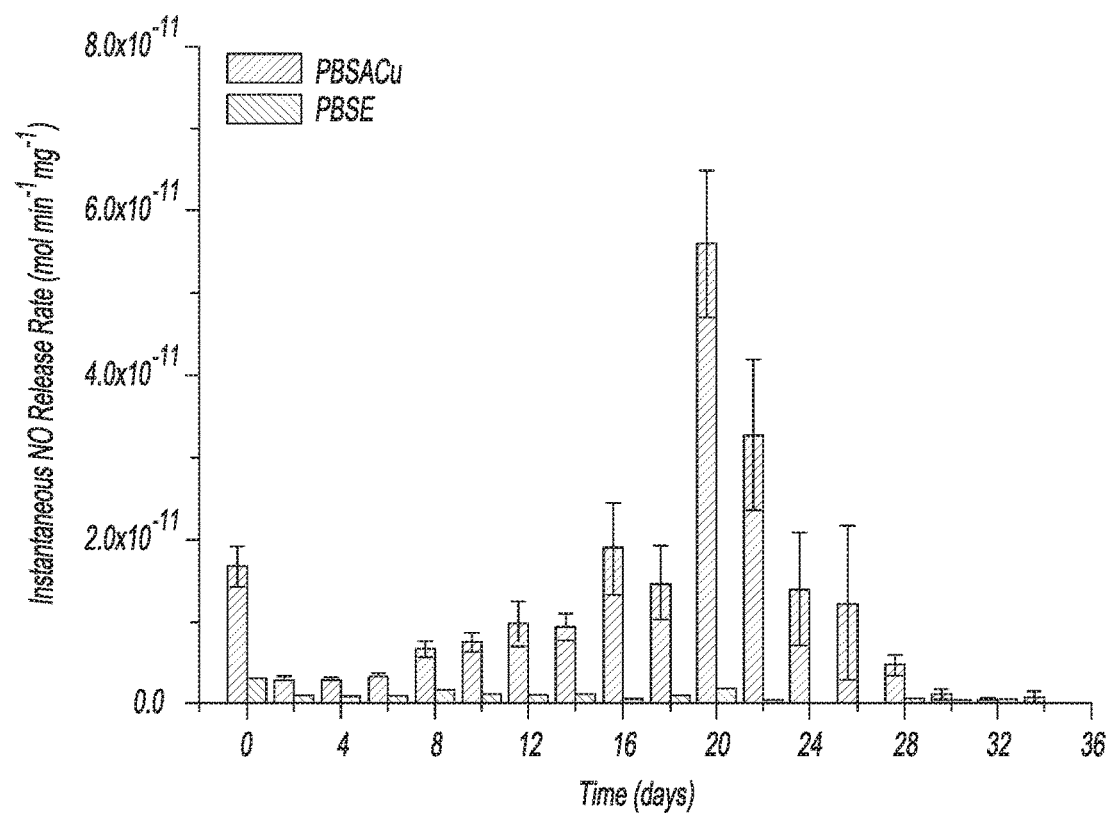

For in vitro monitoring of the NO release from the microspheres, the microspheres were dispersed in the release media within a 50 mL polypropylene centrifuge tube that was placed into a water bath thermostated at 37° C. An amber centrifuge tube was employed to avoid light induced NO photo-release. The emitted NO was purged out from the release media with a continuous nitrogen stream and detected by a chemiluminescence method, which is the gold standard for NO release measurements. The NO concentration of the purged gas was measured until a plateau occurred in the detected NO concentration, which usually took about 0.5 hour. As shown in FIG. 4A and FIG. 4B, the microspheres did not show an initial burst release even in the presence of copper(II) ions and ascorbic acid in the release media (PBSACu), which are known to be initiators for SNAP decomposition. In the presence of EDTA (PBSE), that chelates the copper(II) ions, the NO release was negligible.

Figure 5A:
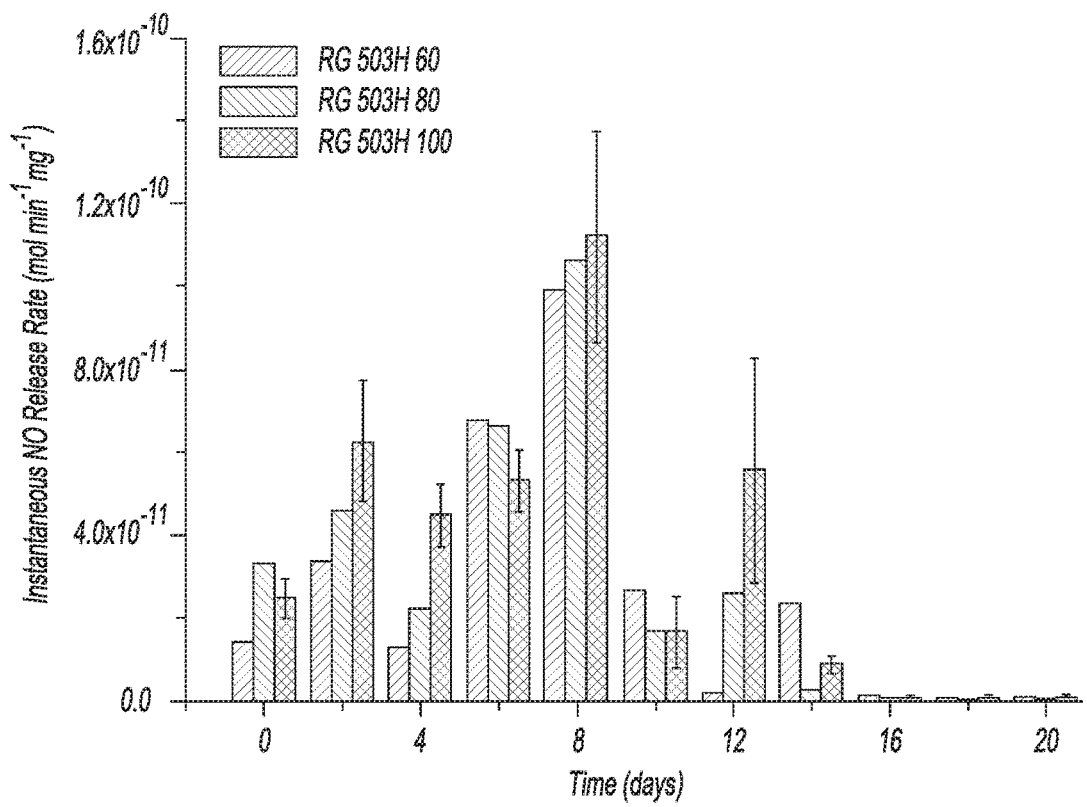
FIGS. 5A-5D are graphs showing instantaneous NO release rates of (FIG. 5A) RG 503H and (FIG. 5C) RG 504 PLGA-SNAP microspheres in PBSACu release media and estimated amount of released NO from (FIG. 5B) RG 503H and (FIG. 5D) RG 504 PLGA-SNAP microspheres in PBSACu release media (note: the NO release is overestimated for RG 503H)
Figure 5B:
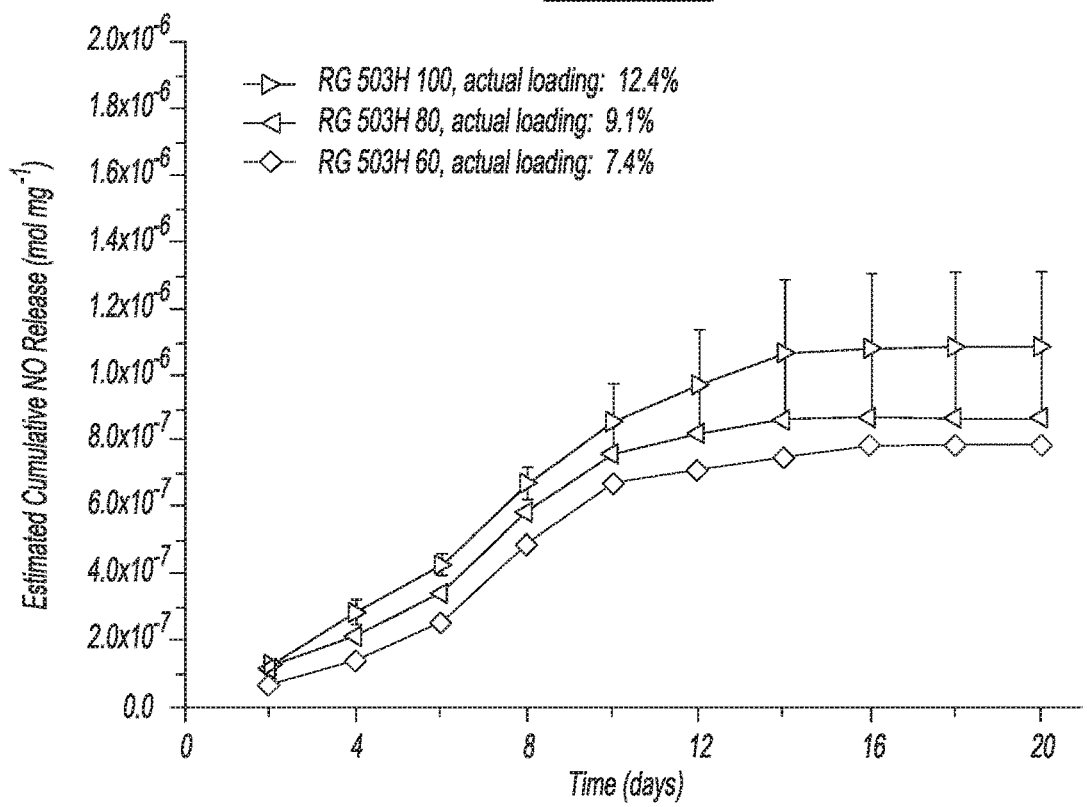
Figure 5C:
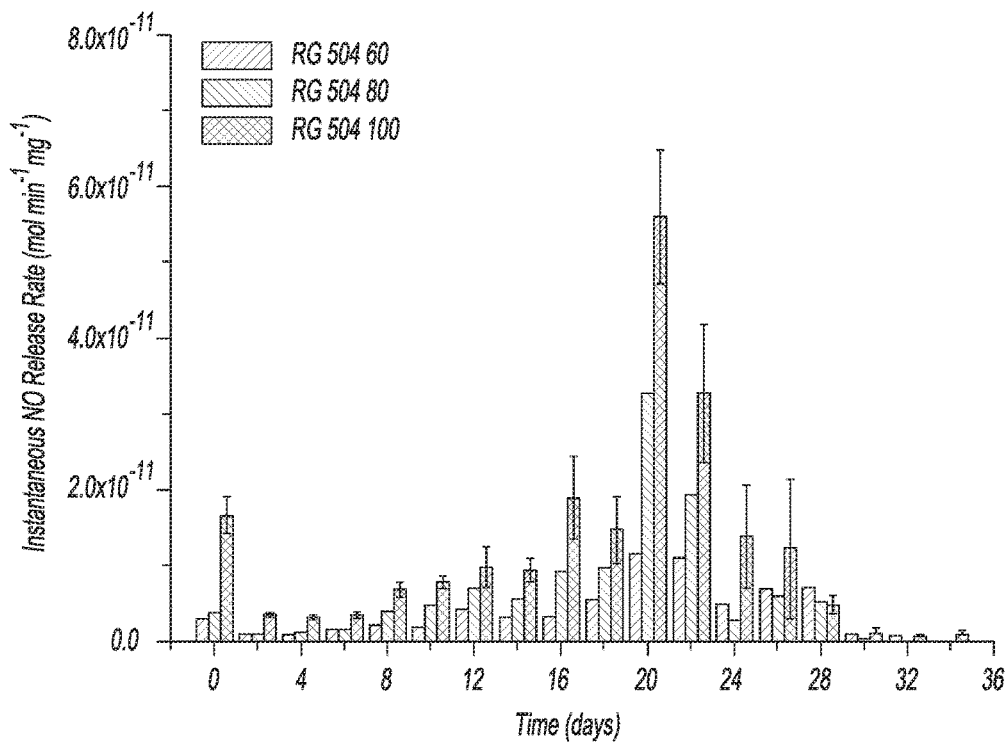
Figure 5D:
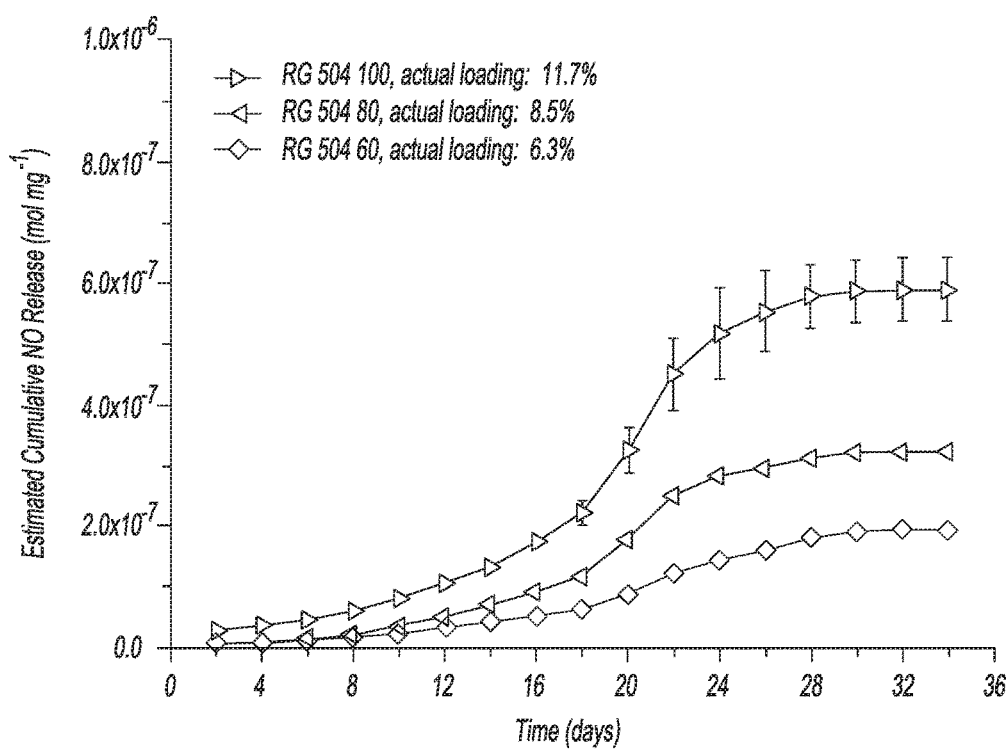
Figure 5E:
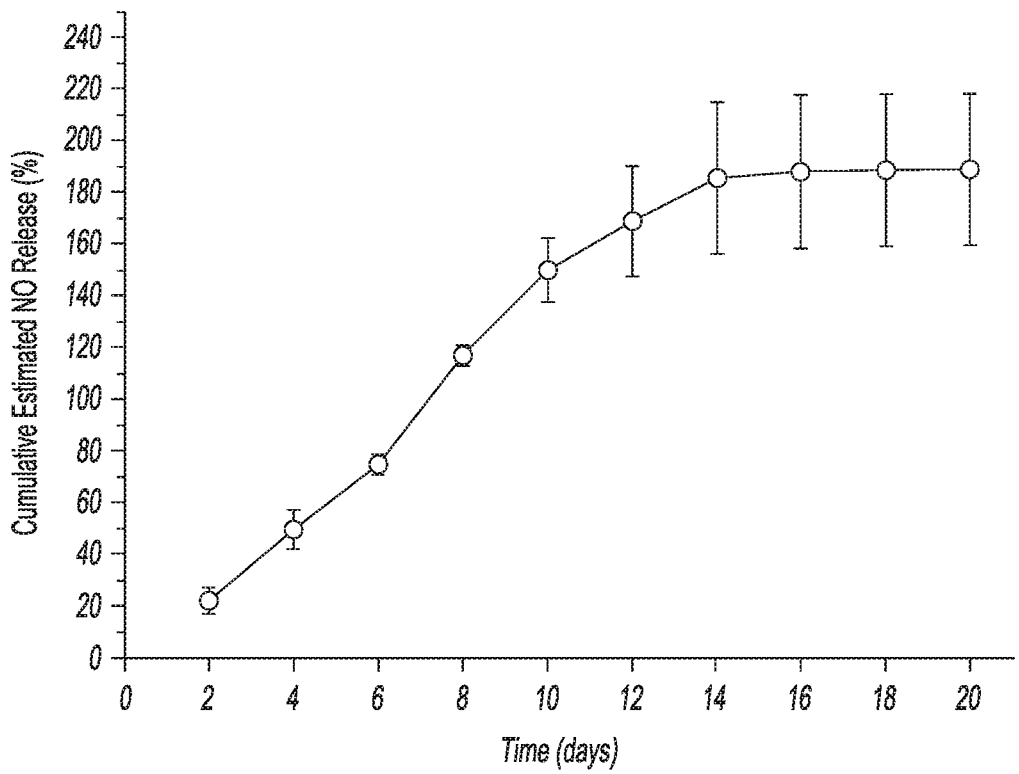
FIGS. 5E and 5F are graphs showing estimated cumulative NO release of (FIG. 5E) RG 503H 100 and (FIG. 5F) RG 504 100 PLGA-SNAP microspheres based on NOA measurements.
Figure 5F:
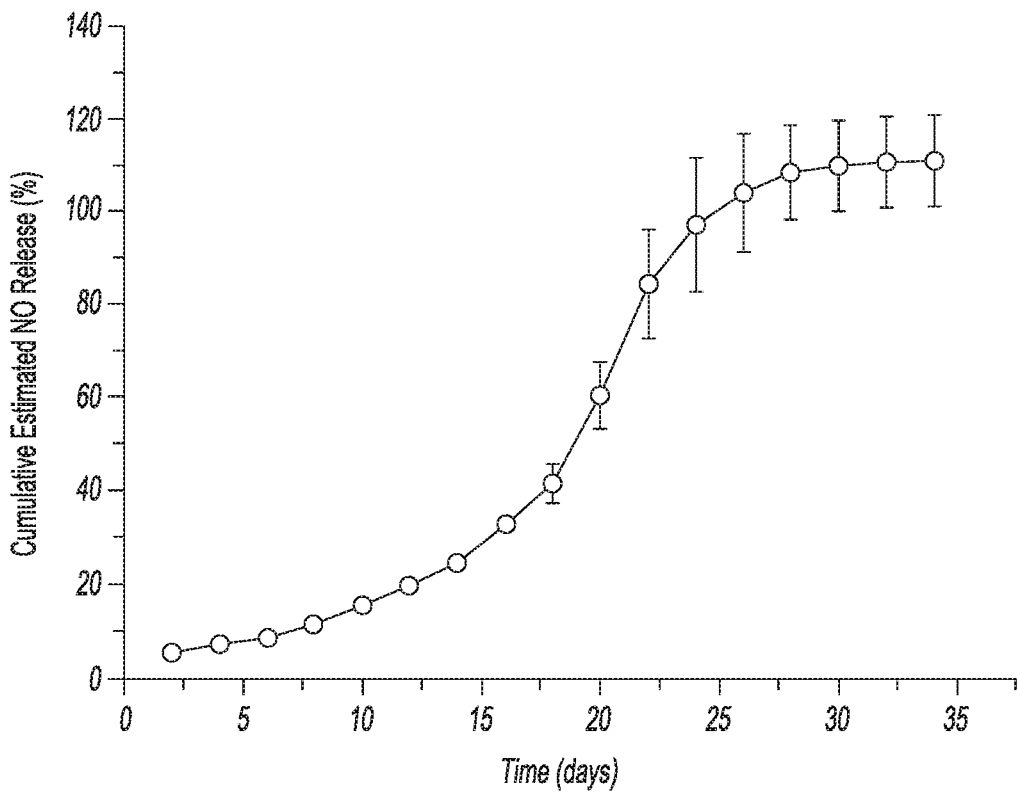

The instantaneous NO release of the PLGA microspheres with different loadings at different time points is shown in FIGS. 5A-5D. In all cases, a significantly higher release rate can be observed just before the measured NO release rates begin to decrease with time. Indeed, the overall NO release is controlled, shown by the estimated cumulative NO release curves (FIGS. 5E and 5F), which were estimated by integrating the instantaneous NO release rates with the trapezoidal rule. The duration of NO release was typically 10-14 days in the case of microspheres prepared with the RG 503H polymer, and about 30 days in the case of the RG 504 microspheres. This correlates well with the expected degradation rates of these two different PLGA polymers. Since the RG 503H has a smaller molecular weight and it is free acid terminated (which increases water content and speeds up the acid catalyzed hydrolysis of the PLGA copolymer), its degradation rate is faster compared to the RG 504, which has a higher molecular weight and an ester capped terminus.

Figure 6:
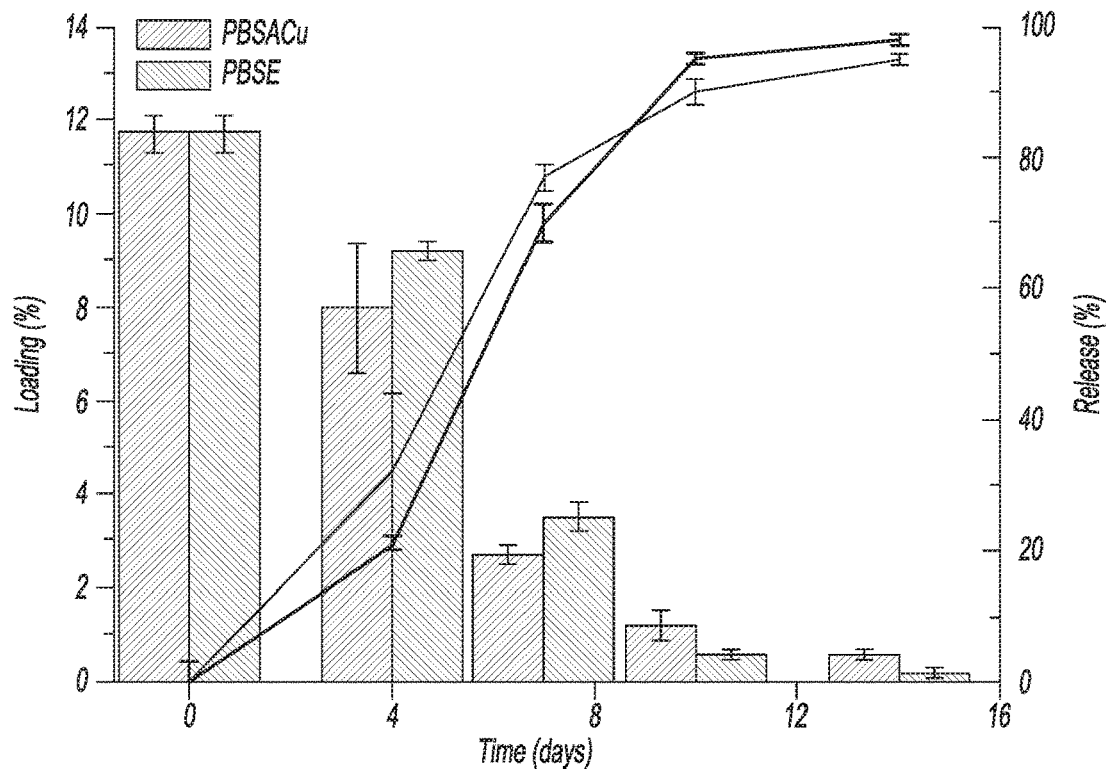
FIG. 6 is a graph showing SNAP loading change (bars) and the SNAP release (lines) of RG 503H 100 PLGA-SNAP incubated in PBSACu and PBSE buffers.

In addition, the absolute value for the NO release rate was tunable as a function of the amount of encapsulated SNAP. It should be pointed out that the estimated cumulative NO release was significantly overestimated in the case of the RG 503H microparticles (see also FIG. 5E). This is probably due to the different conditions used during the NOA measurements (purging with nitrogen) vs. during the incubation of the microspheres in just buffer solution, without purging the NO. To measure the NO release rate, the particles are more intensively mixed and there is essentially no dissolved NO in the solution at any given time (nitrogen purge) that might further decrease the rate of SNAP decomposition. Measuring the remaining SNAP loading in the particles over time demonstrates very similar NO release kinetics, but without the aforementioned measurement error (see FIG. 6). The loading change over time is not significantly different in the PBSACu vs. the PBSE buffer.

The concentration of decomposition product N-acetyl-D-penicillamine disulfide (($NAP)_2$) in the release media was also monitored by RP-HPLC-MS. The leaching of the NO donor and its decomposition products from the microspheres was measured in the soaking buffer by HPLC-MS (Agilent 1200, Agilent 6520 Accurate-Mass Q-TOF LC/MS). A reversed phase (RP) HPLC Method was adapted from Wo et al. (Y. Wo, Z. Li, E. J. Brisbois, A. Colletta, J. Wu, T. C. Major, et al., Origin of long-term storage stability and nitric oxide release behavior of CarboSil polymer doped with S-Nitroso-N-acetyl-D-penicillamine, ACS Applied Materials & Interfaces, 7 (2015) 22218-22227). Briefly, a 10 μL-20 μL aliquot was injected onto the column (Agilent, Eclipse Plus C18, RRHD 1.8 μm, 2.1×50 mm). The elution was performed with 95% water containing 0.1% formic acid and 5% acetonitrile containing 0.1% formic acid for 2 minutes, then with a linear gradient of 95% water containing 0.1% formic acid and 5% acetonitrile containing 0.1% formic acid to 100% acetonitrile containing 0.1% formic acid over a period of 8 minutes. The eluent flow rate was 400 μL/min. The mass spectrometric data were collected in negative ion mode. The negative ions of SNAP, NAP and $(NAP)_2$ (disulfide dimer of NAP) were observed at m/z=190.0543, 219.0445 and 379.1003, respectively, and quantified after calibration of the system with known amounts of these species. The semi-quantitative nature of this measurement was also clarified, which was used simply to determine the continuous nature of NAP release and the time scale that NAP was released.

$(NAP)_2$ leached out continuously during the NO release. After the NO release stopped, a significant amount of $(NAP)_2$ was not seen in the release media after 16 days and 30 days for RG 503H 100 and RG 504 100 formulations, respectively (data not shown). The overall kinetic pattern of release was similar to that described in FIGS. 5A-5D, 6, and 5E-5F, and suggests that the release of $(NAP)_2$ happens approximately at the same time with the NO release. Thus, it seems likely that the location of the SNAP decomposition is within the pores of microspheres formed during the degradation process. Indeed, the degradation of the microspheres was monitored by SEM and correlates well with the release data (see FIGS. 7A-7J). Therefore, in practice, the NO release rate can be controlled by the degradation rate of the PLGA microsphere, since exposure of the encapsulated SNAP species to the aqueous media containing trace copper ions and/or ascorbic acid, is required for NO release. It appears that physiological levels of copper (1 μM) and ascorbate (100 μM) are sufficient to measure physiologically relevant NO release from RG 503H 100 microspheres, that is 10 mg RG 503H 100 microsphere spread over a 1 $cm^2$ area can deliver NO well above the endothelial NO flux rate for about two weeks under physiological conditions (data not shown).

Nitrite is a relatively stable decomposition product of NO. Therefore, NO release of microspheres was also evaluated based on the nitrite concentration within the release media, thus the nitrogen purging effect was avoided.

Twenty five mg microspheres were incubated in 50 mL PBSACu media at 37° C. in a 500 mL flask covered with aluminum foil in order to protect the microspheres from light. One mL samples were taken periodically from the media, and the nitrite concentration was quantified with the chemiluminescent NO analyzer. Since nitrite is a relatively stable product of NO, it can be used for evaluating NO release. A 50 μL sample was injected into acidified KI solution (0.1 M $H_2SO_4$/0.6 M KI), where the nitrite was quantitatively reduced to NO, which can be measured by chemiluminescence.

Figure 8:
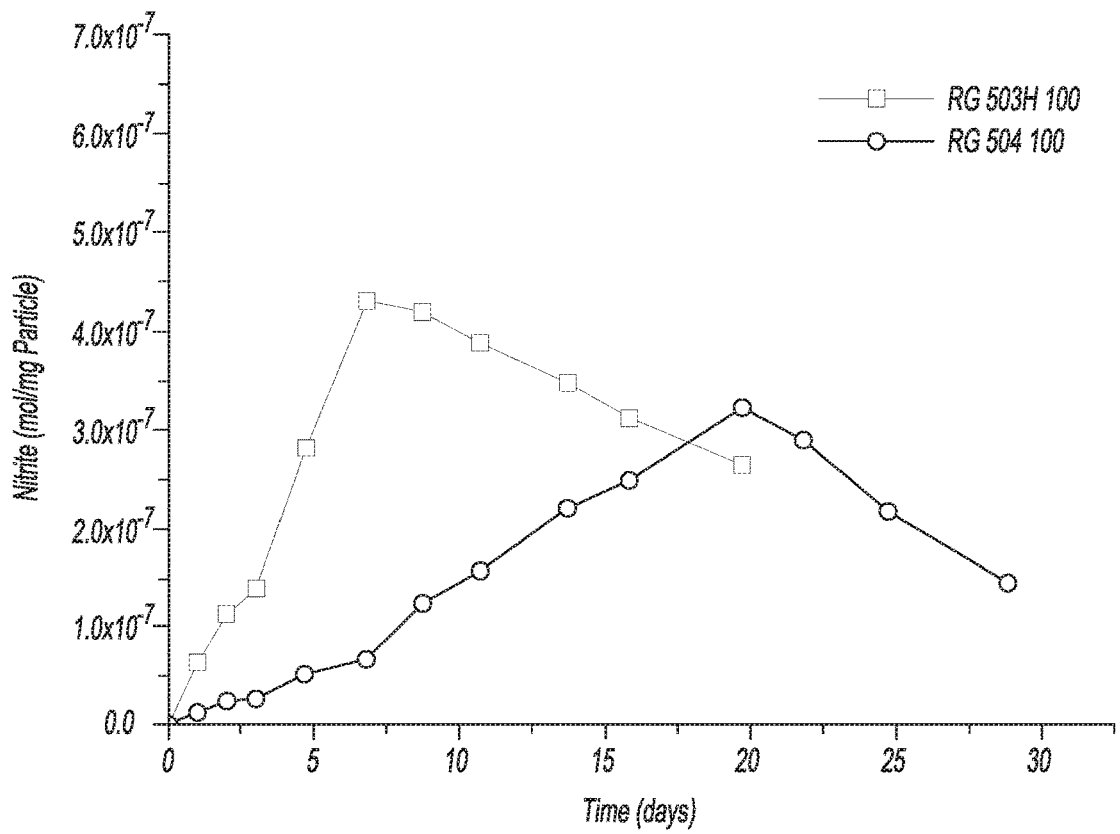
FIG. 8 is a graph showing nitrite concentration of release media with RG 503H 100 (squares) and RG 504 (dots) microspheres, the release media was not purged or changed.
Figures 7A, 7B, 7C, 7D, 7E, 7F, 7G, 7H, 7I, 7J:
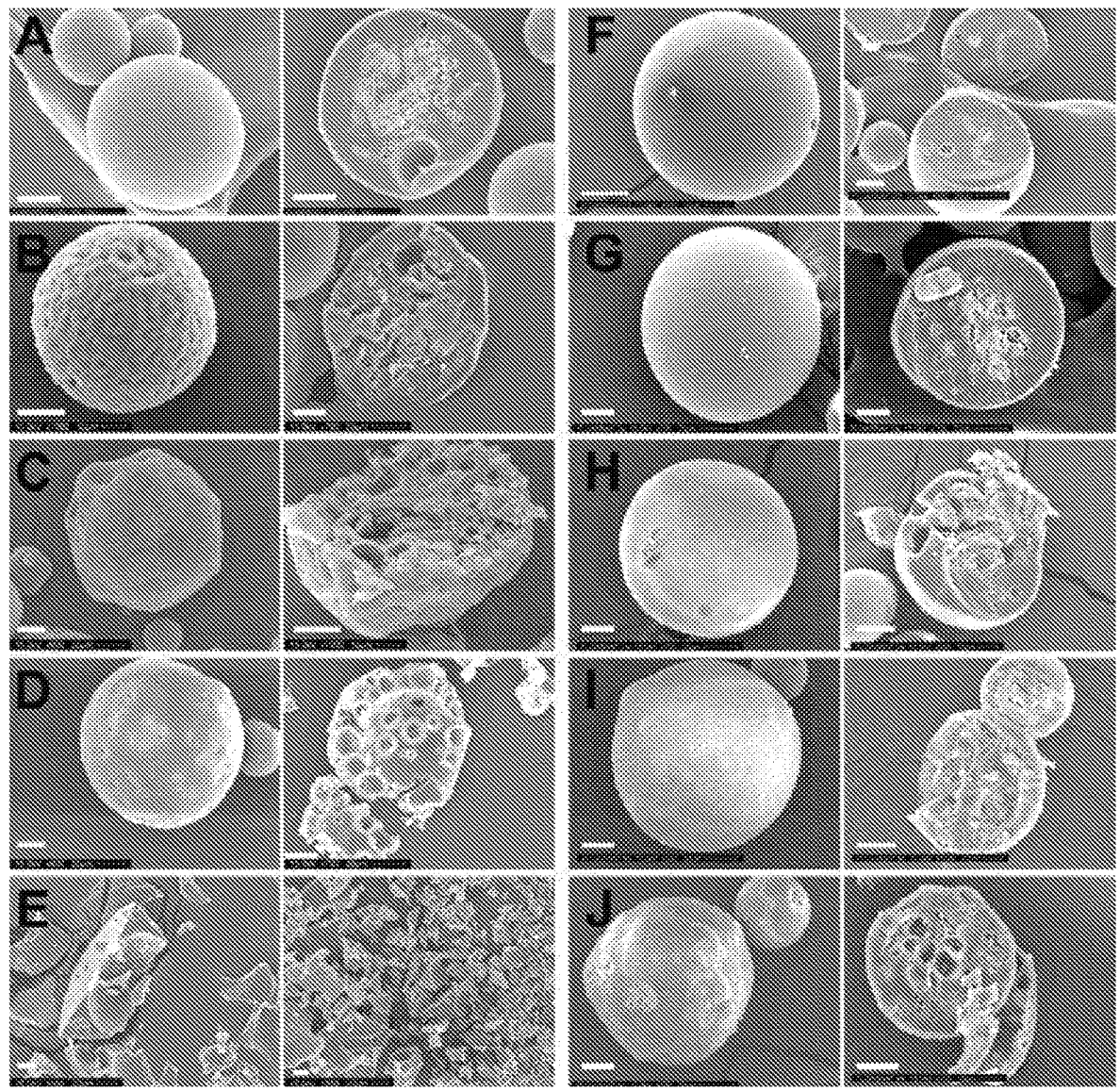
FIGS. 7A-7J are secondary electron micrographs of the surface (left side) and the cross section (right side) of RG 503H PLGA-SNAP microspheres before (FIG. 7A) and after incubation in release media at 37° C. for 4 days (FIG. 7B), 7 days (FIG. 7C), 10 days (FIG. 7D) and 14 days (FIG. 7E), as well RG 504 PLGA-SNAP microspheres before (FIG. 7F) and after incubation in release media at 37° C. for 1 week (FIG. 7G), 2 weeks (FIG. 6H), 3 weeks (FIG. 7I) and 4 weeks (FIG. 7J); the white colored scale bar is 20 μm.

In this case, as shown in FIG. 8, the highest nitrite concentration corresponds to 76% (RG 503H 100) and 62% (RG 504 100) of cumulative release relative to the initial SNAP loading in the microspheres. After reaching a maximum value, the nitrite level within the media (after 5 and 20 days, respectively), the levels of nitrite started decreasing. This may happen since the nitrite is not stable in the increasingly acidic environment produced by the degrading PLGA (nitrite is protonated to $HNO_2$ that can form both $NO_2$ and NO, etc. that will transfer into headspace of the vials containing the media. The slightly shorter release time can be also explained by the fact that release media was not changed during the experiment.

Figure 9A:
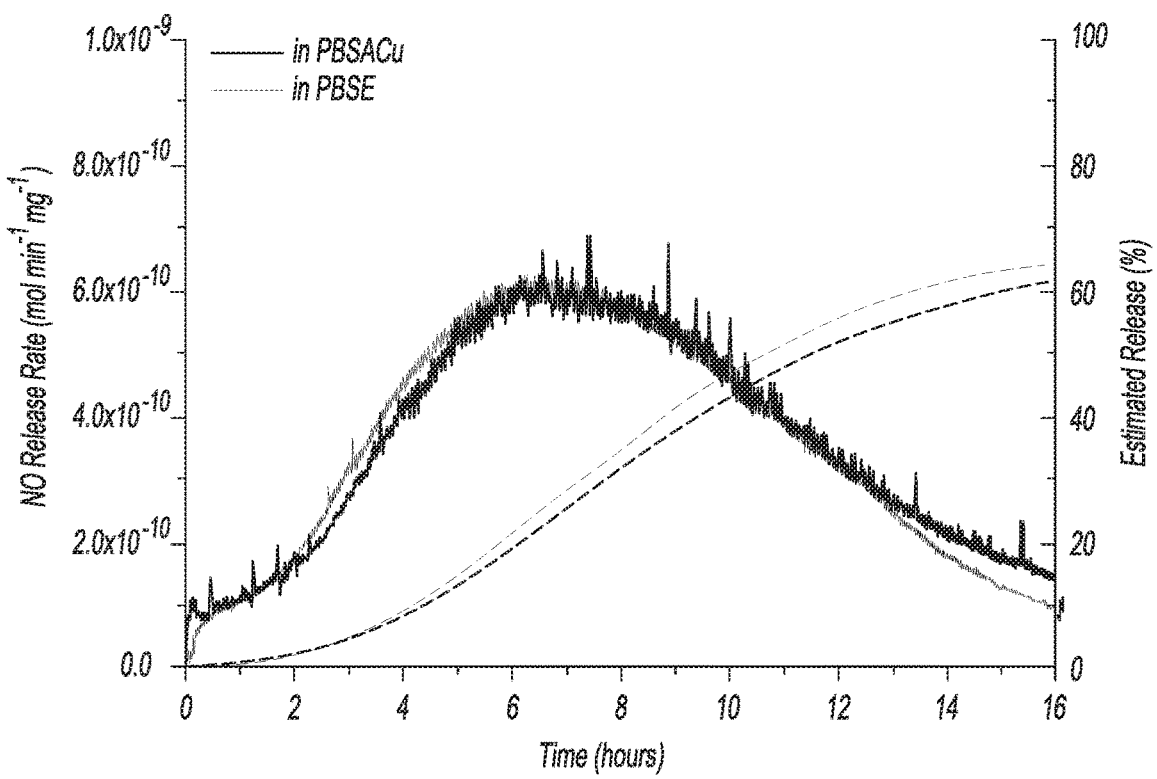
FIGS. 9A and 9B are graphs showing light modulated NO release of (FIG. 9A) RG 503H PLGA-SNAP microspheres in PBSE and in PBSACu release medium and (FIG. 9B) as a dry powder at room temperature; dashed lines show the estimated release in percent.
Figure 9B:
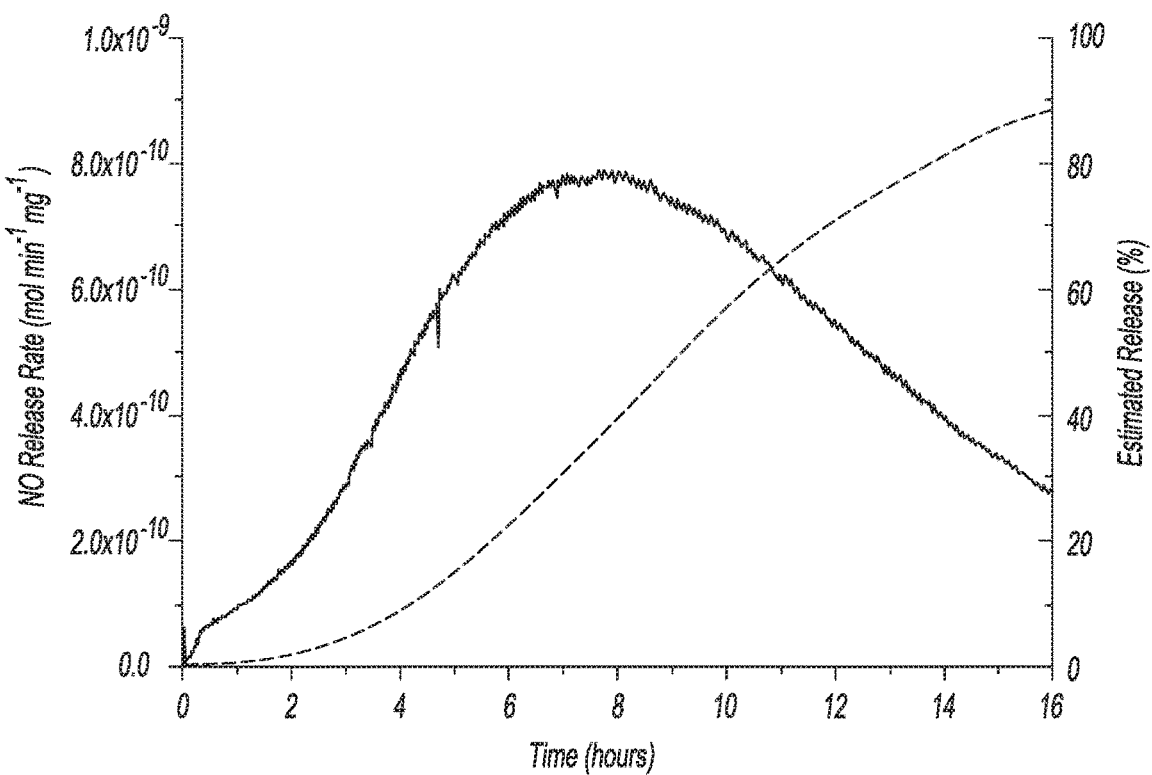

The data provided herein suggests that the main mechanism of NO release is the controlled release of the SNAP species and its immediate decomposition at the interfaces of the microspheres where the necessary copper(II) ions and/or ascorbate are present. However, by shining light directly on the microspheres, another release mechanism is also possible. FIG. 9A and FIG. 9B show the instantaneous NO release by shining light on the dispersed microspheres in two different solutions (FIG. 9A) as well as on the intact dry microspheres (FIG. 9B). Clearly, in this case, no exposure of the SNAP to the soaking solution is required, and the crystals of SNAP within the microspheres are sensitive to the photolysis reaction.

Figure 10:
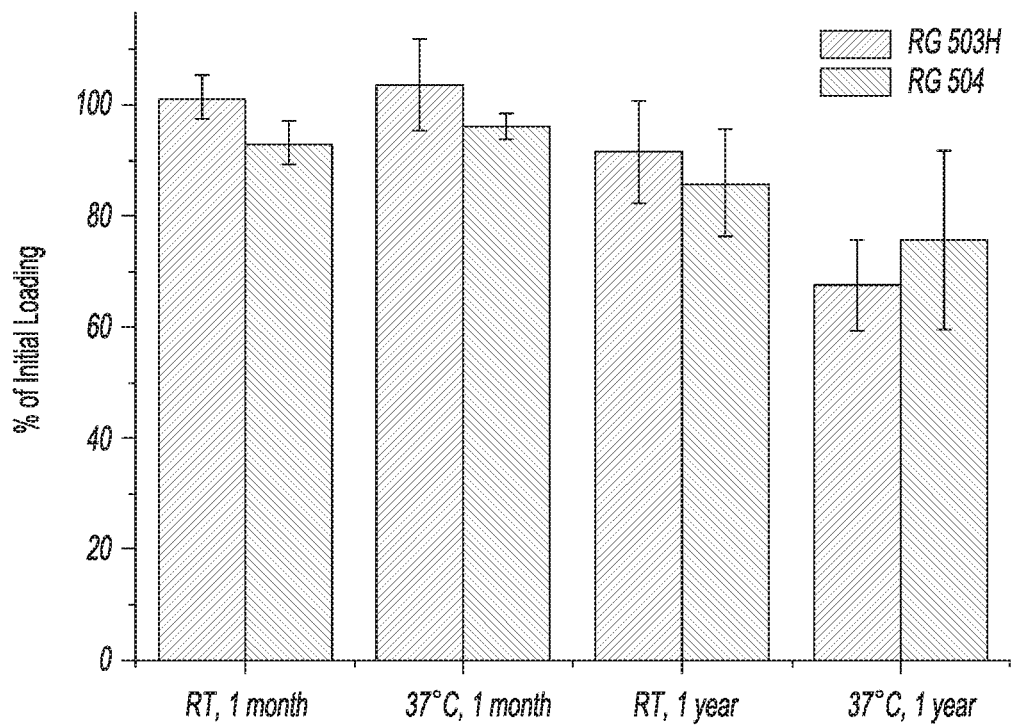
FIG. 10 is a graph showing one month and one year storage stability of RG 504 and RG 503H PLGA-SNAP microspheres at room temperature (RT) and at 37° C., averages and standard deviations are calculated from the loadings of the three formulations for each polymer.

The encapsulated microcrystalline SNAP showed excellent stability also at elevated temperature. Indeed, the SNAP loading did not decrease below 90% after a one-month storage period in the dark (FIG. 10) at room temperature, and even when stored at an elevated temperature of 37° C., there was still ca. 70% of the active NO donor present in the dry microparticles after one year.

PLGA-SNAP In-Vivo Release Study

The present inventors conducted an in-vivo release study of an example PLGA-SNAP RG 504 100 formulation and compared it to the in-vitro release profile.

Methods

PLGA-SNAP formulation "RG 504 100" was prepared as described above. A size fraction between 63 μm and 120 μm was collected and used for the study.

Size distribution was measured by laser diffraction (Mastersizer 2000).

The in-vitro release study was performed as described above, in brief, microspheres were incubated in PBS containing 1 mM ascorbate and 50 μM Cu(II), and at each time point microspheres were washed with DI water, dried and dissolved in acetonitrile. The remaining SNAP content of the microspheres was analyzed by absorbance measured at 340 nm.

For the in-vivo release study, about 30 grams of PLGA-SNAP formulation "RG 504 100" was suspended in a 0.5 mL vehicle solution containing 5% D-mannitol, 0.5% low viscosity carboxymethyl cellulose, 0.1% Tween-80 in DI water, and was injected into a sterile silicone rubber/surgical grade stainless steel mesh (mesh size 37 μm) cage implant system. The mesh allows for free flow of interstitial fluid and cells into the microsphere compartment, while both allowing easy drug release to the animal and retaining the microspheres for quantitative analysis. The cage system has been validated in control studies with two different PLGA microspheres containing triamcinolone and leuprolide where the pharmacokinetics of the drugs was shown to be highly similar after subcutaneous microsphere administration with and without the cage implant. The system was implanted subcutaneously in the backs of healthy male Sprague-Dawley rats. At each time point, animals were sacrificed, cages were retrieved, and the microspheres were collected. After washing the microspheres to remove adhered cells and tissue, microspheres were dissolved in acetonitrile, and SNAP loading was measured by UV/VIS absorbance analysis as described for the in-vitro experiments.

Morphology of retrieved microspheres was analyzed by scanning electron microscope (SEM) using secondary electron mode. After retrieval, the cages containing the microspheres were treated the same way as for the release study.

Results

The initial loading of the 60-125 μm size fraction of PLGA-SNAP RG 504 100 formulation was 11.2 (±0.2)%.

For the study, only the 63 μm-125 μm size fraction of the formulation was used since the mesh size of the applied implant was 37 μm.

TABLE 3

Size distribution of PLGA-SNAP RG 504 100 (63 μm-125 μm) formulation

| | d (0.1) [μm] | d (0.5) [μm] | d (0.9) [μm] | D [4,3] - Volume weighted mean [μm] |
|---|---|---|---|---|
| PLGA-SNAP RG 504 100 (63 μm-125 μm) | 64.2 ± 0.2 | 87.9 ± 0.2 | 119.6 ± 0.2 | 90.1 |

Figure 11:
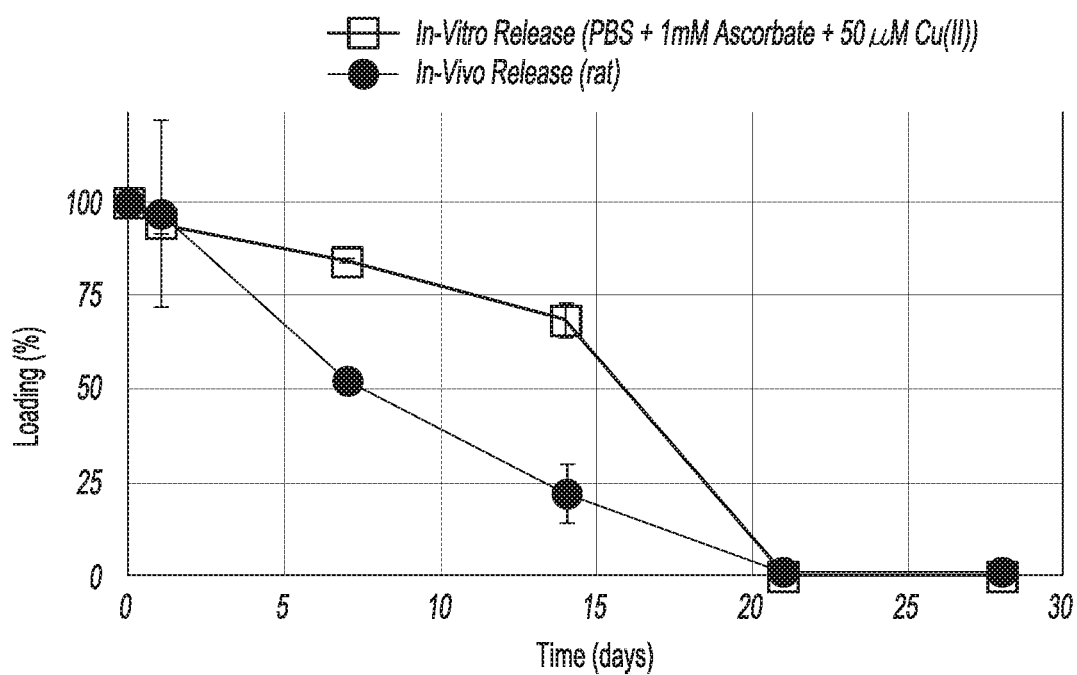
FIG. 11 is a graph showing in-vitro and in-vivo release of SNAP from a PLGA-SNAP RG 504 100 formulation.

The remaining SNAP loading of the PLGA-SNAP formulation decreased steadily for 3 weeks in-vivo. In the first two weeks, faster release was observed compared to in-vitro release. Of note in the in-vitro study, about 70% of the loading was released on the third week. FIG. 11 shows in-vitro and in-vivo release of SNAP from the PLGA-SNAP RG 504 100 formulation.

Figure 12:
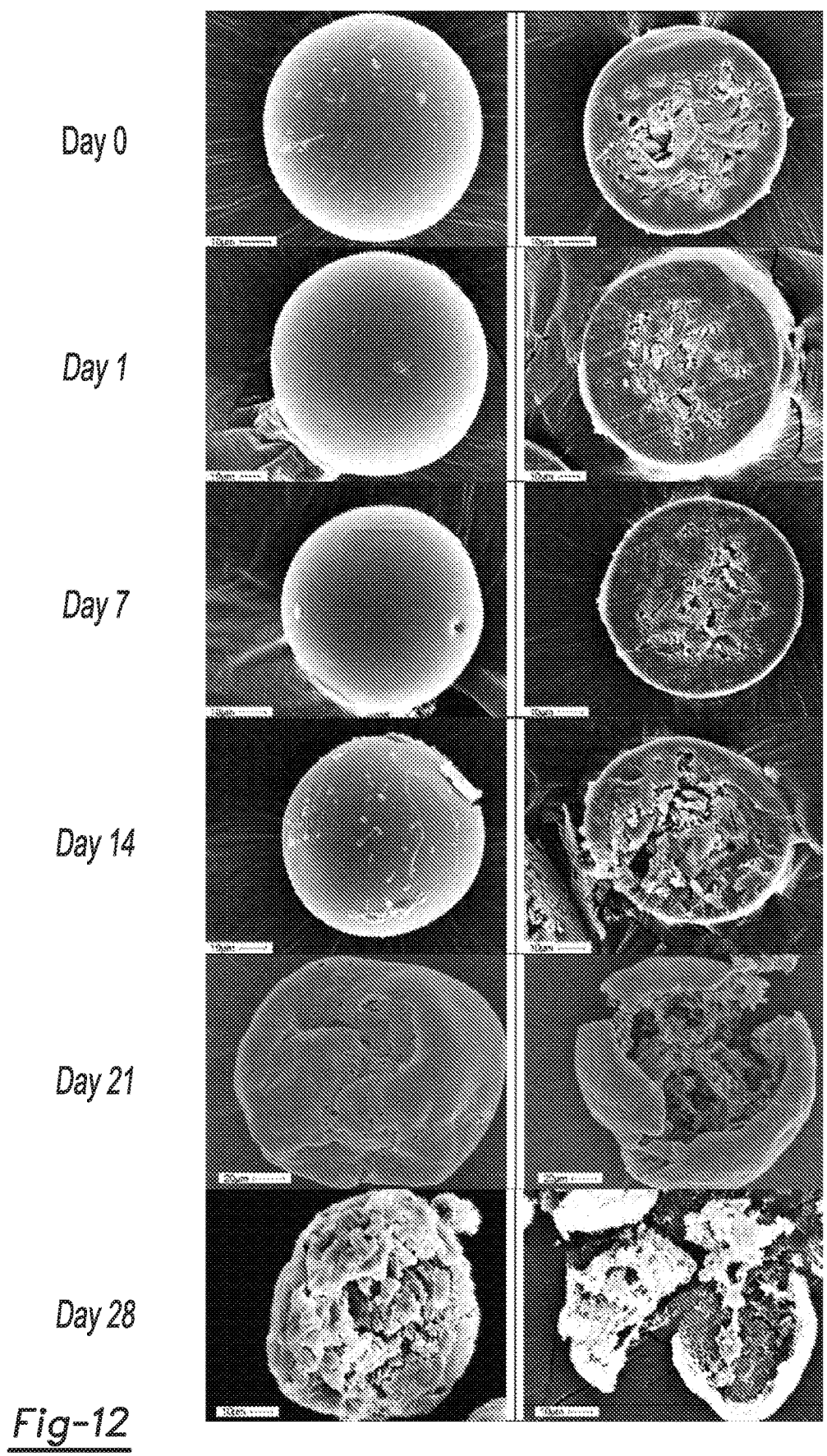
FIG. 12 shows scanning electron micrographs (SEMs) (using secondary electron mode) of PLGA microspheres retrieved from day 0 to day 14 of the in-vivo study.

FIG. 12 is the SEM morphology study, which shows the SNAP crystals entrapped inside the PLGA microspheres from day 0 to day 14 of the in-vivo study. After day 21, the microspheres became very porous, and SNAP crystals could not be identified inside the microspheres.

In this study it has been shown, for the first time, that the NO donor SNAP can be encapsulated into PLGA microspheres using an S/O/W method with high efficiency for long-term controlled release of NO. These microspheres release SNAP in a controlled manner for up to four weeks, and in the presence of copper(II) and ascorbate, the released SNAP is instantaneously decomposed to generate localized NO. The PLGA encapsulated SNAP is highly stable when stored at room temperature for up to 1 year, demonstrating an enhanced shelf-life over many other NO donor systems.

Biomedical Uses of PLGA-SNAP Microspheres

To prepare a new type of NO releasing wound dressing, in an example, the PLGA-SNAP microspheres were incorporated into alginate hydrogel films (PLGA-SNAP/alginate) which can be cross-linked with copper(II) ions. Examples of a PLGA-SNAP/alginate composition can be prepared by dissolving: 1.5% w/v sodium alginate in DI water and 15% glycerol (w/w, based on the mass of alginate) can be added as plasticizer. Subsequently, about 1% (w/v) of PLGA-SNAP microspheres are dispersed in the solution. The dispersion is cast into petri dishes (e.g., 25 mL in an 8.5 cm diameter petri dish) and vacuum dried over a drying agent. Pieces with required shape and size are cut out from the dry film. Before use, they are immersed into a 50 mM $CuCl_2$ solution for 1 minute, washed with DI water and then immersed into 5% (w/v) $CaCl_2$ solution for 5 minutes, then rinsed with DI water again. The PLGA-SNAP/alginate film continuously releases NO at endothelial level over a week period. These PLGA-SNAP/alginate films may be used as wound dressings for skin burns and chronic wounds (e.g., diabetic ulcers, pressure ulcers, etc.), where the antimicrobial and wound healing effects of NO are advantageous.

In a further example, the PLGA-SNAP microspheres may be incorporated into an NO releasing depot injection. The placement of the injection is most commonly to intramuscular or subcutaneous spaces but can be realistically injected in any place in the body accessible by a syringe by a clinician in the office or during surgery. The depot is gradually resorbed by surrounding tissue as the polymer chains are slowly hydrolyzed and the polymer erodes (loses its mass) completely in the body. As an example, a 30 gram PLGA-SNAP formulation is suspended in a 0.5 mL vehicle solution containing 5% D-mannitol, 0.5% low viscosity carboxymethyl cellulose, 0.1% Tween-80 (i.e., polyoxyethylene (20) sorbitan monooleate/polysorbate 80) in DI water; and is injected subcutaneously.

It is to be understood that any ranges provided herein include the stated range and any value or sub-range within the stated range. For example, a range of about 20 μm to about 125 μm should be interpreted to include not only the explicitly recited limits of about 20 μm to about 125 μm, but also to include individual values therebetween, such as 25 microns, 70 microns, 91.4 microns, etc., as well as sub-ranges therebetween, such as from 31 μm to about 111 μm, etc. Furthermore, when "about" is utilized to describe a value, this is meant to encompass minor variations (up to +/−10%) from the stated value.

Reference throughout the specification to "one example", "another example", "an example", and so forth, means that a particular element (e.g., feature, structure, and/or characteristic) described in connection with the example is included in at least one example described herein, and may or may not be present in other examples. In addition, it is to be understood that the described elements for any example may be combined in any suitable manner in the various examples unless the context clearly dictates otherwise.

In describing and claiming the examples disclosed herein, the singular forms "a", "an", and "the" include plural referents unless the context clearly dictates otherwise.

While several examples have been described in detail, it is to be understood that the disclosed examples may be modified. Therefore, the foregoing description is to be considered non-limiting.

What is claimed is:
1. A polymeric composition, consisting of:
poly(lactide-co-glycolide) microspheres or poly(lactic-co-glycolic acid) microspheres; and
S-nitroso-N-acetylpenicillamine (SNAP) or a biodegradable polymer possessing an appended SNAP encapsulated within the poly(lactide-co-glycolide) microspheres or poly(lactic-co-glycolic acid) microspheres by a solid-in-oil-in-water emulsion and solvent evaporation method, wherein the SNAP or the biodegradable polymer possessing the appended SNAP is capable of spontaneously releasing nitric oxide (NO) when exposed to light capable of photolyzing an S-nitrosothiol (RSNO) bond or when exposed to moisture;
the polymeric composition to exhibit stability under dry conditions at 37° C., and prolonged and controllable

NO release rates, when exposed to the light or the moisture, for a predetermined amount of time.

2. The polymeric composition as defined in claim 1 wherein the poly(lactide-co-glycolide) microspheres consist of at least one of: ester capped poly(lactide-co-glycolide) having a 50:50 ratio of lactic acid monomer to glycolic acid monomer; and acid terminated poly(lactide-co-glycolide) having a 50:50 ratio of lactic acid monomer to glycolic acid monomer.

3. The polymeric composition as defined in claim 2 wherein the polymeric composition exhibits sustained NO release under physiological conditions for an amount of time ranging from about 10 days to about 4 weeks.

4. The polymeric composition as defined in claim 1 wherein the poly(lactide-co-glycolide) microspheres or poly(lactic-co-glycolic acid) microspheres each have an average diameter ranging from about 20 μm to about 125 μm.

5. A method for making an NO-releasing polymeric composition, comprising:
encapsulating S-nitroso-N-acetylpenicillamine (SNAP) or a biodegradable polymer possessing an appended SNAP within poly(lactide-co-glycolide) microspheres or poly(lactic-co-glycolic acid) microspheres by a solid-in-oil-in-water emulsion and solvent evaporation method, wherein the SNAP or the biodegradable polymer possessing the appended SNAP is capable of spontaneously releasing nitric oxide (NO) when exposed to light capable of photolyzing an S-nitrosothiol (RSNO) bond or when exposed to moisture;
the polymeric composition to exhibit stability under dry conditions at 37° C., and prolonged and controllable NO release rates, when exposed to the light or the moisture, for a predetermined amount of time.

6. The method as defined in claim 5 wherein:
the SNAP is encapsulated in the poly(lactide-co-glycolide) microspheres; and
the poly(lactide-co-glycolide) microspheres comprise at least one of: ester capped poly(lactide-co-glycolide) having a 50:50 ratio of lactic acid monomer to glycolic acid monomer; and acid terminated poly(lactide-co-glycolide having a 50:50 ratio of lactic acid monomer to glycolic acid monomer.

7. The method as defined in claim 6 wherein the polymeric composition exhibits sustained NO release under physiological conditions for an amount of time ranging from about 10 days to about 4 weeks.

8. An NO releasing wound dressing, comprising:
a hydrogel film; and
the polymeric composition of claim 1 incorporated into the hydrogel film.

9. An NO releasing ointment, comprising:
a hydrophobic ointment; and
the polymeric composition of claim 1 dispersed within the hydrophobic ointment.

10. An NO releasing fluid, comprising:
the fluid including a vehicle, the fluid to be incorporated into a depot injection; and
the polymeric composition of claim 1 incorporated into the vehicle.

11. A method for making an NO releasing wound dressing, comprising:
dispersing the polymeric composition of claim 1 in an alginate solution to form a dispersion;
casting the dispersion into a mold; and
drying the cast dispersion to form a layer of a polymer microsphere-alginate composite film; and
crosslinking the composite film to form a hydrogel wound dressing material.

12. The polymeric composition as defined in claim 1 wherein the SNAP is encapsulated within the poly(lactide-co-glycolide) microspheres or poly(lactic-co-glycolic acid) microspheres, and wherein an amount of encapsulated SNAP ranges from about 0.3 μmol per mg microsphere to about 0.6 μmol per mg microsphere.

13. The polymeric composition as defined in claim 1 wherein the SNAP is encapsulated within the poly(lactide-co-glycolide) microspheres or poly(lactic-co-glycolic acid) microspheres.

14. The polymeric composition as defined in claim 1 wherein the biodegradable polymer possessing the appended SNAP is encapsulated within the poly(lactide-co-glycolide) microspheres or poly(lactic-co-glycolic acid) microspheres, and wherein the biodegradable polymer is selected from the group consisting of polylactide, polyglycolide (PGA), polycaprolactone, copolymers thereof, and mixtures thereof.

15. The polymeric composition as defined in claim 13 wherein the SNAP is non-dissolved, crystalline SNAP.

16. The polymeric composition as defined in claim 15 wherein a loading of the SNAP does not decrease below 90% after a one-month storage period in dark conditions at room temperature.

17. The polymeric composition as defined in claim 15 wherein a loading of the SNAP does not decrease below 70% after a one year storage period in dark conditions at 37° C.

* * * * *